(12) United States Patent
Hosono et al.

(10) Patent No.: US 11,174,217 B2
(45) Date of Patent: Nov. 16, 2021

(54) POLYMERIZABLE COMPOUND AND LIQUID CRYSTAL COMPOSITION

(71) Applicant: DIC Corporation, Tokyo (JP)

(72) Inventors: Ayaki Hosono, Kitaadachi-gun (JP); Masanao Hayashi, Kitaadachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 16/615,503

(22) PCT Filed: May 29, 2018

(86) PCT No.: PCT/JP2018/020478
§ 371 (c)(1),
(2) Date: Nov. 21, 2019

(87) PCT Pub. No.: WO2018/230322
PCT Pub. Date: Dec. 20, 2018

(65) Prior Publication Data
US 2020/0087240 A1    Mar. 19, 2020

(30) Foreign Application Priority Data

Jun. 12, 2017  (JP) .............................. JP2017-115118

(51) Int. Cl.
*C07C 69/54*     (2006.01)
*C07D 319/06*   (2006.01)
*C09K 19/56*     (2006.01)

(52) U.S. Cl.
CPC ............ *C07C 69/54* (2013.01); *C07D 319/06* (2013.01); *C09K 19/56* (2013.01); *B32B 2457/20* (2013.01); *B32B 2457/202* (2013.01); *C07C 2601/16* (2017.05); *C09K 2323/00* (2020.08)

(58) Field of Classification Search
CPC ... C07C 69/54; C07C 2601/16; C07C 233/20; C07C 323/25; C07D 319/06; C09K 19/56; C09K 2323/00; C09K 2019/0448; C09K 2019/122; B32B 2457/20; B32B 2457/202; C07F 7/081
See application file for complete search history.

(56) References Cited

U.S. PATENT DOCUMENTS

| 3,210,327 | A |  | 10/1965 | Graliano et al. |
| 3,280,078 | A |  | 10/1966 | Hostettler et al. |
| 3,532,715 | A |  | 10/1970 | Hostettler et al. |
| 3,755,420 | A |  | 8/1973  | Stoffey et al. |
| 3,774,305 | A |  | 11/1973 | Stoffey et al. |
| 4,962,163 | A |  | 10/1990 | Hefner, Jr. et al. |
| 5,919,599 | A |  | 7/1999  | Meador et al. |
| 5,998,499 | A |  | 12/1999 | Klee et al. |
| 6,458,908 | B1 |  | 10/2002 | Imai et al. |
| 6,906,116 | B2 |  | 6/2005  | Nishikubo et al. |
| 7,541,071 | B2 |  | 6/2009  | Shundo et al. |
| 9,458,264 | B2 |  | 10/2016 | Aoshima et al. |
| 9,725,590 | B2 |  | 8/2017  | Chun et al. |
| 2006/0054859 | A1 | * | 3/2006 | Shundo ............. C09K 19/3861 252/299.01 |
| 2010/0296032 | A1 |  | 11/2010 | Shin et al. |
| 2014/0018517 | A1 |  | 1/2014  | Busygin et al. |
| 2014/0138581 | A1 |  | 5/2014  | Archetti et al. |
| 2014/0175342 | A1 |  | 6/2014  | Uchikawa |
| 2015/0252265 | A1 | * | 9/2015 | Archetti ................ C09K 19/04 349/130 |
| 2016/0137921 | A1 | * | 5/2016 | Hayashi ............. C09K 19/3861 252/299.62 |
| 2016/0362606 | A1 | * | 12/2016 | Tong ....................... C07C 67/08 |
| 2017/0158793 | A1 | * | 6/2017 | Endo ................... C08F 220/303 |
| 2017/0210994 | A1 | * | 7/2017 | Lim .................... C09K 19/3402 |
| 2019/0308926 | A1 | * | 10/2019 | Lan ....................... C07C 69/618 |

FOREIGN PATENT DOCUMENTS

| CN | 1236115 A | 11/1999 |
| CN | 100341852 C | 10/2007 |
| CN | 106397752 A | 2/2017 |
| FR | 1434145 A | 4/1966 |

(Continued)

OTHER PUBLICATIONS

International Search Report dated Aug. 28, 2018, issued in counterpart International Application No. PCT/JP2018/020478 (5 pages).

(Continued)

*Primary Examiner* — Eli D. Strah
(74) *Attorney, Agent, or Firm* — Westerman, Hattori, Daniels & Adrian, LLP

(57) ABSTRACT

A compound represented by formula (i) has, as $K^{i1}$ in the formula (i), a structure represented by any one of formula (K-1) to formula (K-3). When used in a liquid crystal composition, it adheres to substrates which hold the liquid crystal composition (liquid crystal layer) therebetween, thereby permitting liquid crystal molecules to be maintained in the state of being aligned in the vertical direction. The liquid crystal composition using the compound enables liquid crystal molecules to be aligned even when the PI layer is not provided (vertical alignment of liquid crystal molecules is induced without the voltage applied and horizontal alignment of liquid crystal molecules is realized with the voltage applied). It is possible to provide a polymerizable compound being excellent in storability and capable of uniform vertical alignment of liquid crystal molecules with no PI layer provided.

10 Claims, No Drawings

(56) References Cited

FOREIGN PATENT DOCUMENTS

| | | |
|---|---|---|
| JP | 2-173031 A | 7/1990 |
| JP | 2-232602 A | 9/1990 |
| JP | 2-240128 A | 9/1990 |
| JP | 3-244615 A | 10/1991 |
| JP | 4-4215 A | 1/1992 |
| JP | 4-316890 A | 11/1992 |
| JP | 7-92674 A | 4/1995 |
| JP | 7-206974 A | 8/1995 |
| JP | 9-157340 A | 6/1997 |
| JP | 2001-509128 A | 7/2001 |
| JP | 2002-502982 A | 1/2002 |
| JP | 2002-123921 A | 4/2002 |
| JP | 2002-145935 A | 5/2002 |
| JP | 2003-138223 A | 5/2003 |
| JP | 2005-206579 A | 8/2005 |
| JP | 2009-215189 A | 9/2009 |
| JP | 2011-514542 A | 5/2011 |
| JP | 2012-008223 A | 1/2012 |
| JP | 2012-242701 A | 12/2012 |
| JP | 2013-542297 A | 11/2013 |
| JP | 2014-524951 A | 9/2014 |
| JP | 2015-155532 A | 8/2015 |
| JP | 2015-535814 A | 12/2015 |
| KR | 10-2016-0115000 A | 10/2016 |
| WO | 2002/018313 A1 | 3/2002 |
| WO | 2002/064662 A1 | 8/2002 |
| WO | 2009/091225 A2 | 7/2009 |
| WO | 2013/047523 A1 | 4/2013 |
| WO | 2014/007361 A1 | 1/2014 |
| WO | 2014/106799 A2 | 7/2014 |
| WO | 2015/198915 A1 | 12/2015 |
| WO | WO-2015198915 A1 * | 12/2015 ........... G02B 5/3016 |

OTHER PUBLICATIONS

Nishikubo et al., "Synthesis of Photocrosslinkable Hyperbranched Polyesters with Terminal Methacryloyl Groups by the One-pot Polyaddition of Bis(oxetane)s with 1,3,5-Benzenetricarboxylic Acid and Methacrylic Acid", Polymer Journal (Tokyo, Japan), 2006, vol. 38, No. 5, p. 447-456, ISSN:0032-3896, cited in ISR (10 pages).

Registry [online], US: American Chemical Society [retrieved on Jul. 9, 2018], Retrieved from: STN, CAS RN 2089601-61-4;2089601-60-3; 2089601-57-8; 2089601-55-6; 2089601-53-4; 2089601-51-2; 2089601-49-8 2089601-47-6; 2089601-46-5;2089601-37-4, cited in ISR.

Fujisawa et al., "Mechanisms of Action of (Meth)acrylates in Hemolytic Activity, in Vivo Toxicity and Dipalmitoylphosphatidylcholine (DPPC) Liposomes Determined Using NMR Spectroscopy", Int. J. Mol. Sci. 2012, v.13, pp. 758-773 (16 pages).

Sun, Xiao-Hong et al., "Diffraction measurement and analysis of slanted holographic polymer dispersed liquid crystal", American Institute of physics, 2005, v.98, pp. 043510-1 to 5; Cited in JP Office Action dated Jan. 14, 2020. (6 pages).

\* cited by examiner

POLYMERIZABLE COMPOUND AND LIQUID CRYSTAL COMPOSITION

TECHNICAL FIELD

The present invention relates to a polymerizable compound, a liquid crystal composition, and a liquid crystal display device.

BACKGROUND ART

A VA-mode liquid crystal display has included a polyimide alignment film (PI) provided on an electrode in order to induce vertical alignment of liquid crystal molecules without the voltage applied and to realize horizontal alignment of liquid crystal molecules with the voltage applied. However, much cost is required for forming a film of the PI layer, and thus a method for realizing alignment of liquid crystal molecules while omitting the PI layer has recently been investigated.

For example, Patent Literature 1 discloses a liquid crystal medium containing a mixture of polar compounds having negative dielectric anisotropy as a base and at least one self-alignment additive, and describes that the liquid crystal medium is highly suitable for use in displays containing no alignment layer. In addition, Patent Literature 1 uses a specified compound having a hydroxyl group as a self-alignment additive.

CITATION LIST

Patent Literature

PTL 1: Japanese Unexamined Patent Application Publication (Translation of PCT Application) No. 2014-524951

SUMMARY OF INVENTION

Technical Problem

However, according to the research performed by the inventors, it was found that when the self-alignment additive described in Patent Literature 1 is used, electrooptical characteristics such as alignment regulating force for vertically aligning liquid crystal molecules, alignment unevenness, etc. are still unsatisfactory, and there is a room for improvement in storability of a liquid crystal composition containing the self-alignment additive.

Therefore, an object of the present invention is to provide a polymerizable compound which can secure storability when added to a liquid crystal composition and which has a polar group capable of aligning liquid crystal molecules with no PI layer provided. Another object of the present invention is to provide a liquid crystal composition excellent in storability and capable of vertically aligning liquid crystal molecules with no PI layer provided and to provide a liquid crystal display device using the liquid crystal composition.

Solution to Problem

The present invention provides a compound represented by general formula (i).

[Chem. 1]

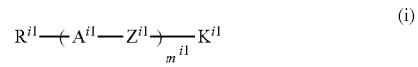

(i)

(In the formula, $R^{i1}$ each independently represent a hydrogen atom, a linear or branched alkyl group having 1 to 40 carbon atoms, an alkyl halide group, or $P^{i1}$-$Sp^{i1}$-, in which —$CH_2$— in the alkyl group may be substituted by —CH=CH—, —C≡C—, —O—, —NH—, —COO—, or —OCO— so that oxygen atoms are not directly adjacent to each other; $A^{i1}$ represents a single bond, a divalent 6-membered aromatic cyclic group, a divalent 6-membered aromatic heterocyclic group, a divalent 6-membered aliphatic cyclic group, or a divalent 6-membered aliphatic heterocyclic group, in which a hydrogen atom in the cyclic structure may be substituted by a halogen atom, $P^{i1}$-$Sp^{i1}$-, a monovalent organic group having a substituent represented by $K^{i1}$, $K^{i1}$, or $R^{i1}$; $Z^{i1}$ represents a single bond, —CH=CH—, —CF=CF—, —C≡C—, —COO—, —OCO—, —OCOO—, —OOCO—, —$CF_2$O—, —$OCF_2$—, —CH=CHCOO—, —OCOCH=CH—, —CH=C($CH_3$)COO—, —OCOC($CH_3$)=CH—, —$CH_2$—CH($CH_3$)COO—, —OCOCH($CH_3$)—$CH_2$—, —$OCH_2CH_2O$—, or an alkylene group having 2 to 20 carbon atoms, in which one or two or more nonadjacent —$CH_2$— in the alkylene group may be substituted by —O—, —COO—, or —OCO—; $K^{i1}$ represents a group represented by any one of general formulae (K-1) to (K-3); $X^{K1}$ and $Y^{K1}$ each independently represent —$CH_2$—, an oxygen atom, or a sulfur atom; $Z^{K1}$ represents an oxygen atom or a sulfur atom; $S^1$, $S^3$, $S^4$, and $S^5$ each represent an alkyl group having 1 to 6 carbon atoms or a single bond; $S^2$ represents C, N, or Si; $X^1$ and $X^2$ each represent OH, $NH_2$, $NHR^{i1}$, CHO, COOH, SH, $R^{i1}$, or P, but any one of these represents OH, $NH_2$, $NHR^{i1}$, CHO, COOH, or SH; P and $P^{i1}$ each represent a polymerizable group; $Sp^{i1}$ represents a spacer group or a single bond; $m^{i1}$ represents an integer of 1 to 4; n represents 0 or 1; when a plurality of each of $R^{i1}$, $A^{i1}$, $Z^{i1}$, $K^{i1}$, $X^{K1}$, $Y^{K1}$, $Z^{K1}$, $S^1$, $S^2$, $S^3$, $S^4$, $S^5$, $P^{i1}$, $Sp^{i1}$, and n are present in the general formula (i), they may be the same or different; and when $S^4$ represents a single bond and $X^1$ represents OH, n is 1.)

[Chem. 2]

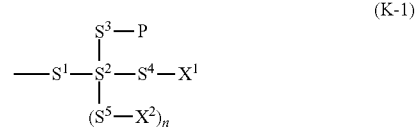

(K-1)

(K-2)

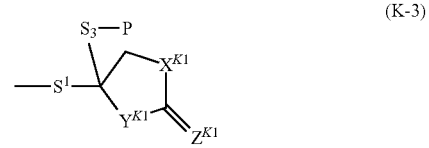

(K-3)

In addition, the present invention provides a liquid crystal composition containing one or two or more compounds represented by the general formula (i).

Advantageous Effects of Invention

According to the present invention, it is possible to provide a polymerizable compound excellent in storability and capable of uniformly vertically aligning liquid crystal molecules with no PI layer provided, and to provide a liquid crystal composition and a liquid crystal display device using the liquid crystal composition.

DESCRIPTION OF EMBODIMENTS

A polymerizable compound according to an embodiment of the present invention is a compound represented by general formula (i).

[Chem. 3]

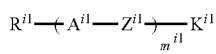

(i)

In the general formula (i), $K^{i1}$ represents a group represented by any one of formulae (K-1) to (K-3) below.

[Chem. 4]

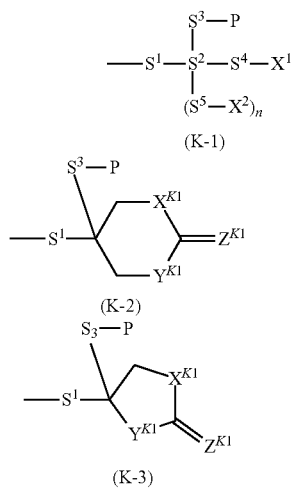

A compound represented by the general formula (i) has a partial structure, particularly, represented by any one of the general formula (K-1) to (K-3), and thus when used in a liquid crystal composition, the compound is aligned between substrates which sandwich the liquid crystal composition (liquid crystal layer) therebetween, and liquid crystal molecules can be held in the state of being aligned in the vertical direction. Therefore, the liquid crystal composition using the polymerizable compound according to the embodiment of the present invention can align liquid crystal molecules (induce vertical alignment of liquid crystal molecules without the voltage applied and realize horizontal alignment of liquid crystal molecules with the voltage applied) with no PI layer provided. Thus, the compound (i) is preferably used for supporting the vertical alignment of liquid crystal molecules in the liquid crystal composition.

In addition, the inventors of the present invention found that the polymerizable compound represented by the formula (i) according to the embodiment has the partial structure represented by any one of the general formulae (K-1) to (K-3), and thus not only alignment of liquid crystal molecules but also storage stability of the liquid crystal composition can be secured.

From the above viewpoint, the polymerizable compound according to the embodiment may have the partial structure represented by any one of the general formulae (K-1) to (K-3) at a molecular end, preferably a molecular main-chain end, and the chemical structure of a bond site to which the partial structure represented by any one of the general formulae (K-1) to (K-3) is bonded is not particularly limited within a range where the function of the liquid crystal composition is not inhibited.

In the general formula (i), $K^{i1}$ is an important structure for vertically aligning the liquid crystal composition, and thereby good alignment can be achieved due to adjacent polar and polymerizable groups, and good solubility in the liquid crystal composition is exhibited. When reliability is regarded as important, polyfunctionalization can be easily attempted by introducing a polymerizable group into an $A^{i1}$ part, and a strong polymer can be constructed. When the alignment of liquid crystal is regarded as important, the general formula (K-1) is preferred, while when the solubility in a liquid crystal compound is regarded as important, the general formula (K-2) and the general formula (K-3) are preferred. $S^1$, $S^3$, $S^4$, and $S^5$ are each preferably an alkyl group having 1 to 3 carbon atoms and a single bond, $S^2$ is preferably carbon, and $X^{K1}$ and $Y^{K1}$ are each preferably an oxygen atom. $Z^{K1}$ represents an oxygen atom or a sulfur atom, but from the viewpoint of VHR, an oxygen atom is preferred. $X^1$ and $X^2$ are each preferably —OH, —CHO, —COOH, —SH, or —P and particularly preferably OH. n represents 0 or 1, but preferably represents 1. When n represents 0 and $S^2$ represents C or Si, $S^2$ represents CH or SiH.

Preferred examples of the general formulae (K-1) to (K-3) include (K-1-1) to (K-1-10) below, but in view of alignment and reactivity, the formulae (K-1-1), (K-2-, (K-1-2) to (K-1-4), (K-3-1), and (K-1-10) are preferred, and the formulae (K-1-1), (K-2-1), (K-1-3), and (K-1-4) are particularly preferred.

[Chem. 5]

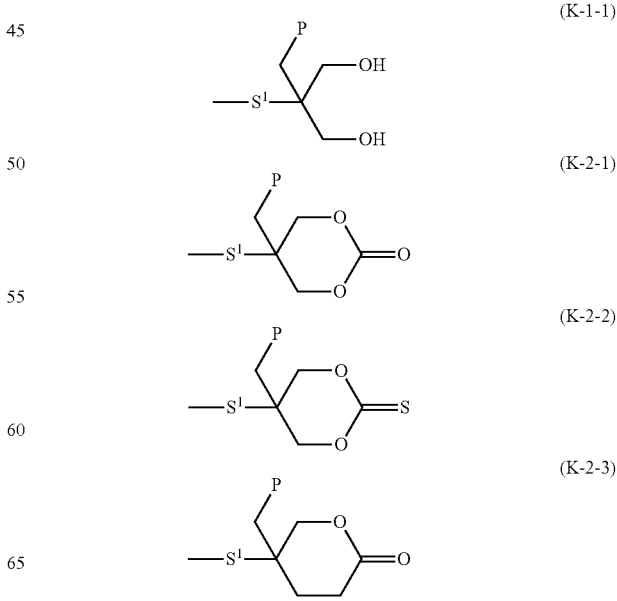

-continued
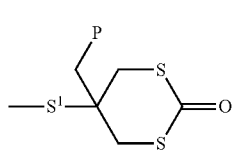
(K-2-4)
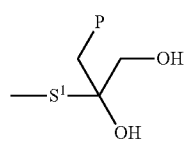
(K-1-2)
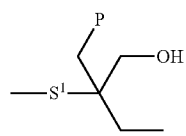
(K-1-3)
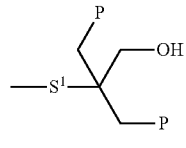
(K-1-4)
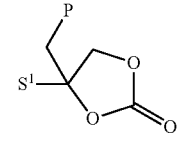
(K-3-1)
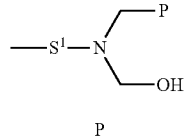
(K-1-5)
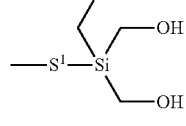
(K-1-6)
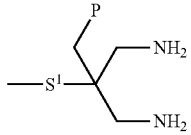
(K-1-7)
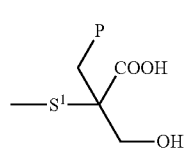
(K-1-8)
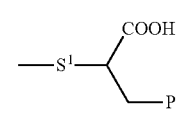
(K-1-9)
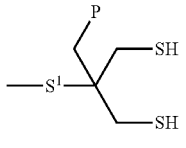
(K-1-10)
In the formula (i), P and $P^{i1}$ preferably each independently represent a substituent selected from the group represented by general formula (P-1) to general formula (P-14) below. In view of easy handling and reactivity, the formulae (P-1) and (P-2) are more preferred.
[Chem. 6]
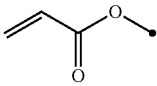
(P-1)
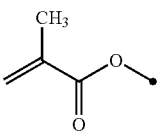
(P-2)
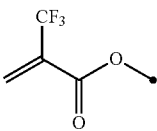
(P-3)
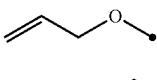
(P-4)
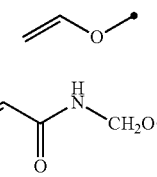
(P-5)
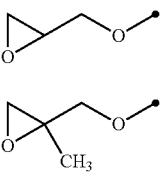
(P-6)
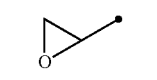
(P-7)
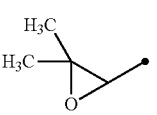
(P-8)
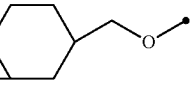
(P-9)
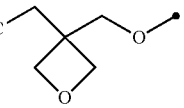
(P-10)
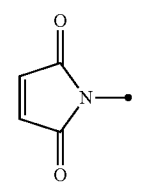
(P-11)
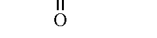
(P-12)
(P-13)

(P-14)

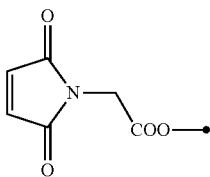

(In the formulae, a black point at the right end represents a bond.)

In the formula (i), $Sp^{i1}$ preferably represents a linear alkylene group having 1 to 18 carbon atoms or a single bond, more preferably presents a linear alkylene group having 2 to 15 carbon atoms or a single bond, and still more preferably represents a linear alkylene group having 2 to 8 carbon atoms or a single bond.

In the formula (i), $Z^{i1}$ preferably represents a single bond, —CH=CH—, —C≡C—, —COO—, —OCO—, —OCOO—, —OOCO—, —CH=CHCOO—, —OCOCH=CH—, —CH=C(CH$_3$)COO—, —OCOC(CH$_3$)=CH—, —CH$_2$—CH(CH$_3$)COO—, —OCOCH(CH$_3$)—CH$_2$—, —OCH$_2$CH$_2$O—, a linear or branched alkylene group having 1 to 40 carbon atoms, or a group in which one or two or more nonadjacent —CH$_2$— in the alkylene group is substituted by —O—, more preferably represents a single bond, —COO—, —OCO—, —CH=CHCOO—, —OCOCH=CH—, —CH=C(CH$_3$)COO—, —OCOC(CH$_3$)=CH—, —CH$_2$—CH(CH$_3$)COO—, —OCOCH(CH$_3$)—CH$_2$—, —OCH$_2$CH$_2$O—, a linear or branched alkylene group having 1 to 10 carbon atoms, or a group in which one or two or more nonadjacent —CH$_2$— in the alkylene group is substituted by —O—, more preferably represents a single bond, a linear alkylene group having 2 to 15 carbon atoms, or a group in which one or two or more nonadjacent —CH$_2$— in the alkylene group is substituted by —O—, and still more preferably represents a single bond, —COO—, —OCO—, —OCOO—, —OOCO—, —OCH$_2$CH$_2$O—, an alkylene group (an ethylene group (—CH$_2$CH$_2$—)) having 2 carbon atoms, a group (—CH$_2$O— or —OCH$_2$—) in which one —CH$_2$— in the ethylene group is substituted by —O—, or a group (—CH—CHCOO— or —OCOCH—CH—) in which one —CH$_2$— in the ethylene group is substituted by —COO— or —OCO—.

$R^{i1}$ preferably represents a hydrogen atom, a linear or branched alkyl group having 1 to 20 carbon atoms, an alkyl halide group, or P-Sp-, in which —CH$_2$— in the alkyl group is preferably substituted by —O—, —OCO—, —COO—, or —C=C— (where —O— is not continued), and more preferably represents a linear or branched alkyl group having 1 to 18 carbon atoms or $P^{i1}$-$Sp^{i1}$-, in which —CH$_2$— in the alkyl group may be substituted by —O— or —OCO— (where —O— is not continued).

$A^{i1}$ preferably represents a single bond or a group having a cyclic structure selected from a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indane-2,5-diyl group, a 1,2,3,4-tetrahydronaphthalene-2,6-diyl group, and a 1,3-dioxane-2,5-diyl group, in which the cyclic structure may be unsubstituted or substituted by an alky group having 1 to 12 carbon atoms, an alkyl halide group having 1 to 12 carbon atoms, an alkoxy group having 1 to 12 carbon atoms, an alkoxy halide group having 1 to 12 carbon atoms, a halogen atom, a cyano group, a nitro group, or $P^{i1}$-$Sp^{i1}$-. $A^{i1}$ preferably represents a divalent 6-membered aromatic cyclic group or a divalent 6-membered aliphatic cyclic group, is preferably a divalent unsubstituted 6-membered aromatic cyclic group, a divalent unsubstituted 6-membered aliphatic cyclic group, or a group in which a hydrogen atom in the cyclic structure is substituted by an alkyl group having 1 to 6 carbon atoms, an alkoxy group having 1 to 6 carbon atoms, a halogen atom, or P-Sp-, is preferably a divalent unsubstituted 6-membered aromatic cyclic group, a group in which a hydrogen atom in the cyclic structure is substituted by a fluorine atom, or a divalent unsubstituted 6-membered aliphatic cyclic group, and is more preferably a 1,4-phenylene group, a 2,6-naphthalene group, or a 1,4-cyclohexyl group in which a hydrogen atom on a substituent may be substituted by a halogen atom, an alkyl group, an alkoxy group, or P-Sp-. $m^{i1}$ preferably represents an integer of 2 to 5, and more preferably represents an integer of 2 or 3.

P represents a polymerizable group, and the polymerizable group P is preferably a substituent of any one of (P-1) to (P-3), (P-13), and (P-14).

In the general formula (i), "$Z^{i1}$—$S^1$—" which is a connecting part between $Z^{i1}$ and $S^1$ in $K^{i1}$ preferably represents —O—(CH$_2$)n-, —(CH$_2$)n-O—(CH$_2$)m-, —COO—(CH$_2$)n-, or —OCO—(CH$_2$)n- (n and m each represent an integer of 1 to 6).

More specific examples of the general formula (i) include, but are not limited to, formulae (R-1-1) to (R-1-25) below.

[Chem. 7]

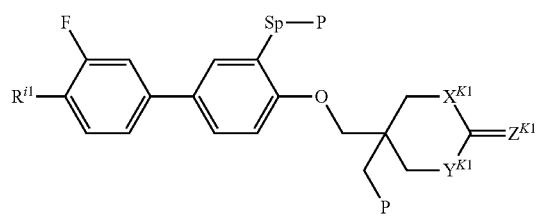

(R-1-1)

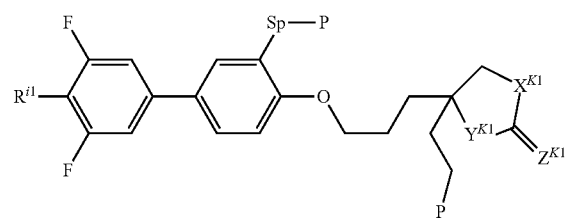

(R-1-2)

-continued
(R-1-3)
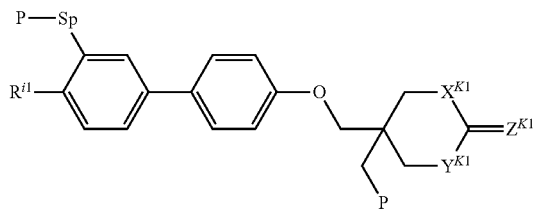
(R-1-4)
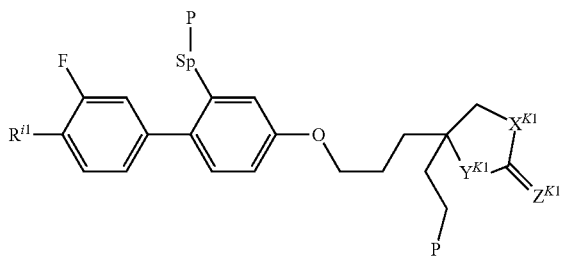
(R-1-5)
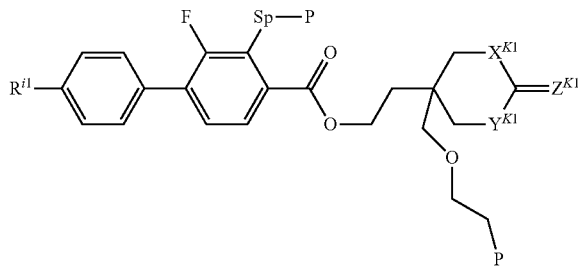
(R-1-6)
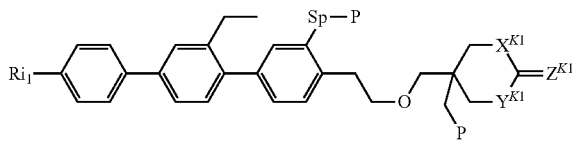
(R-1-7)
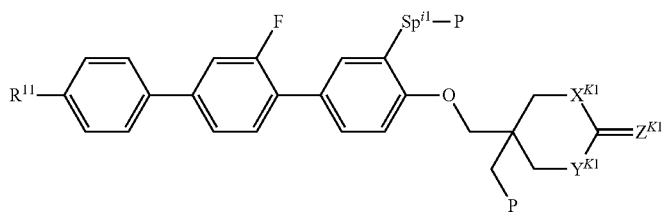
[Chem. 8]
(R-1-8)
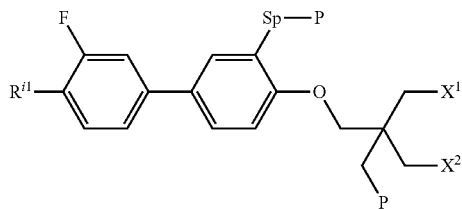
(R-1-9)
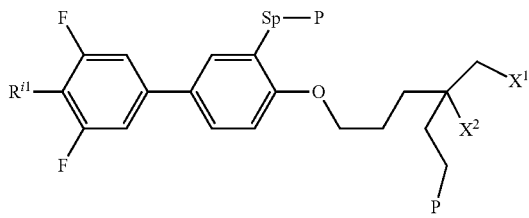
(R-1-10)
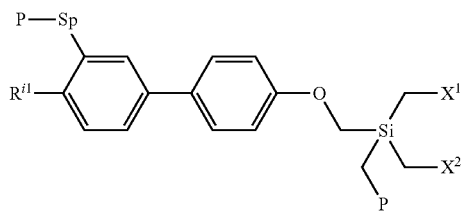
(R-1-11)
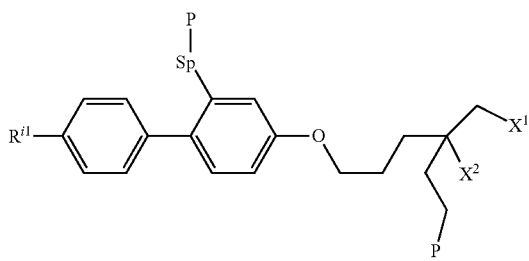
(R-1-12)
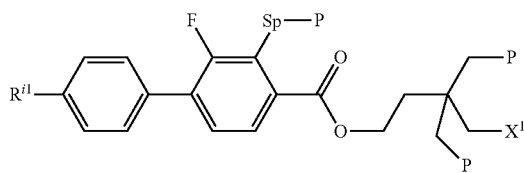
(R-1-13)
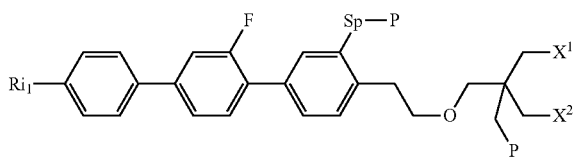

-continued
(R-1-14)
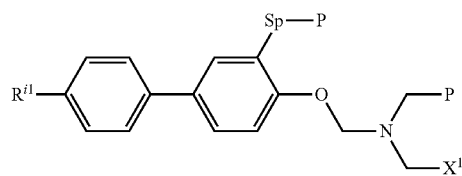
[Chem. 9]
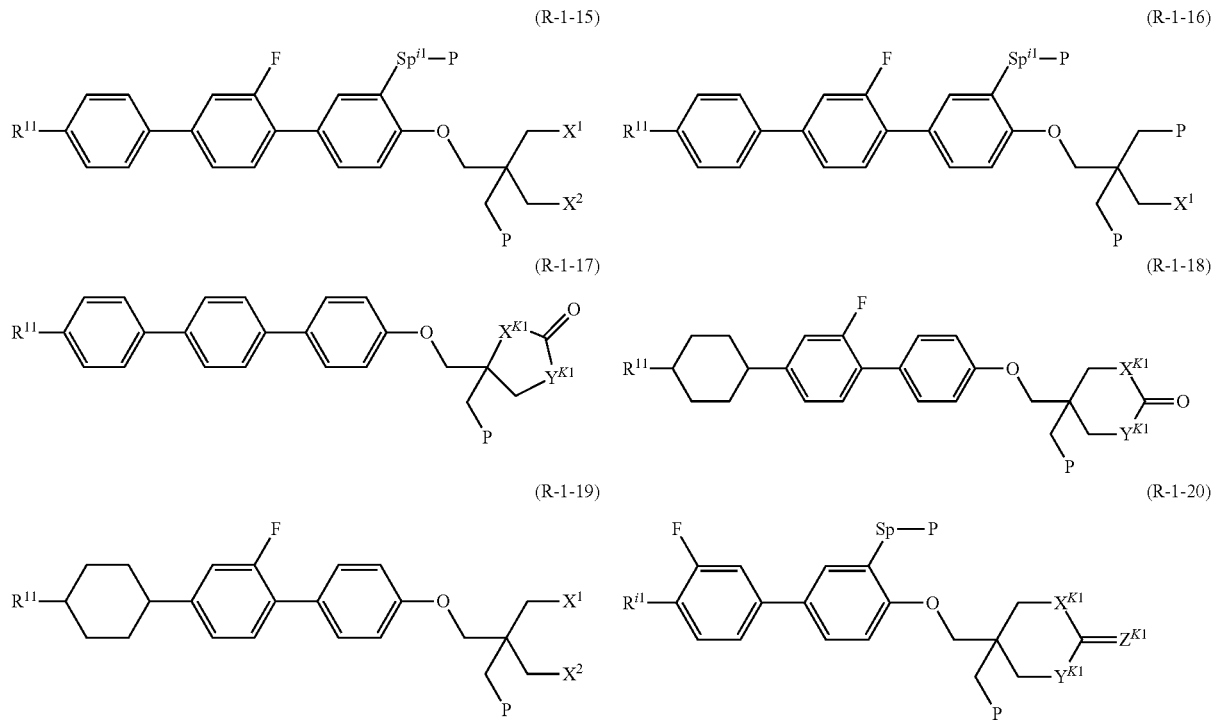
[Chem. 10]
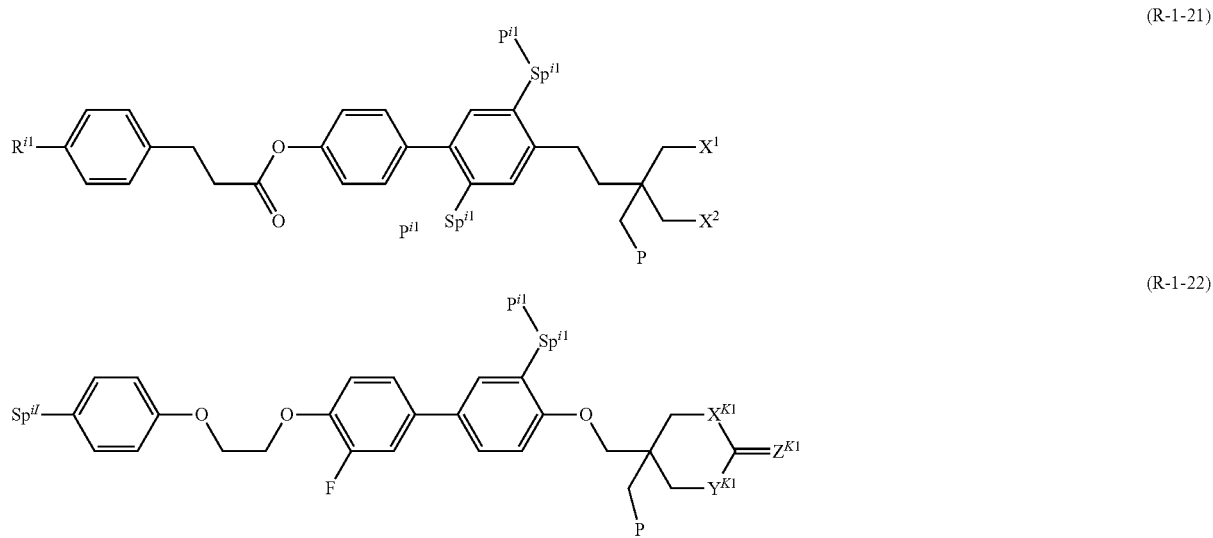

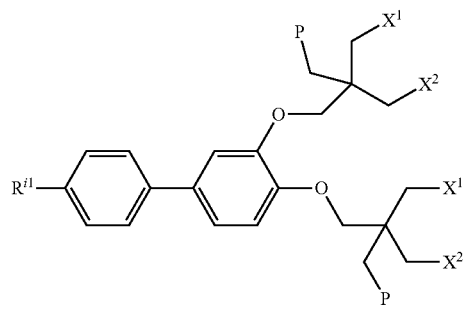
(R-1-23)
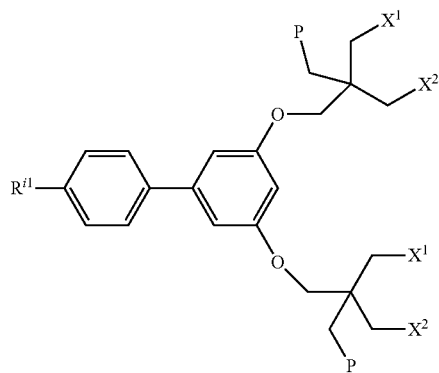
(R-1-24)
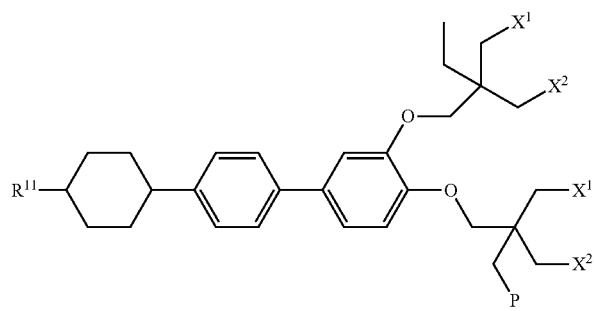
(R-1-25)
More specific examples of a compound represented by the general formula (i) include (P-1-1) to (P-1-27) below.
[Chem. 11]
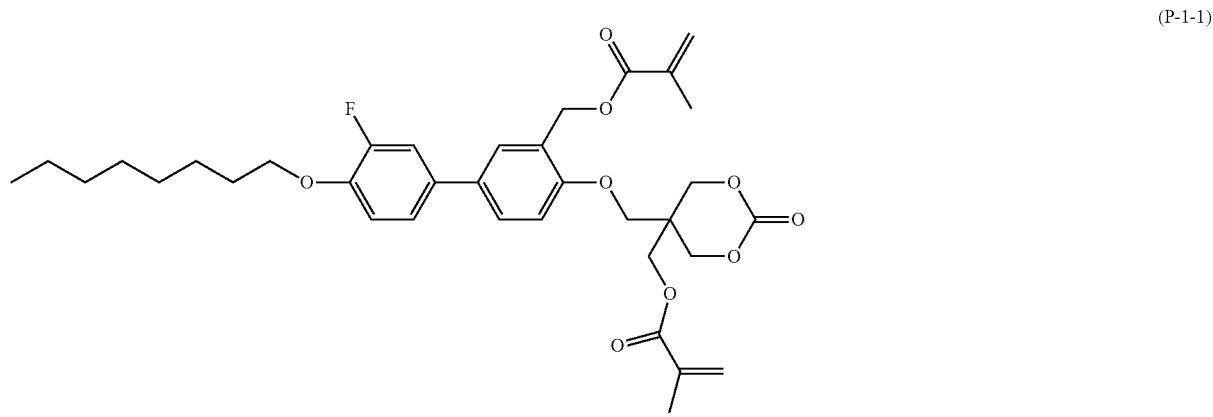
(P-1-1)
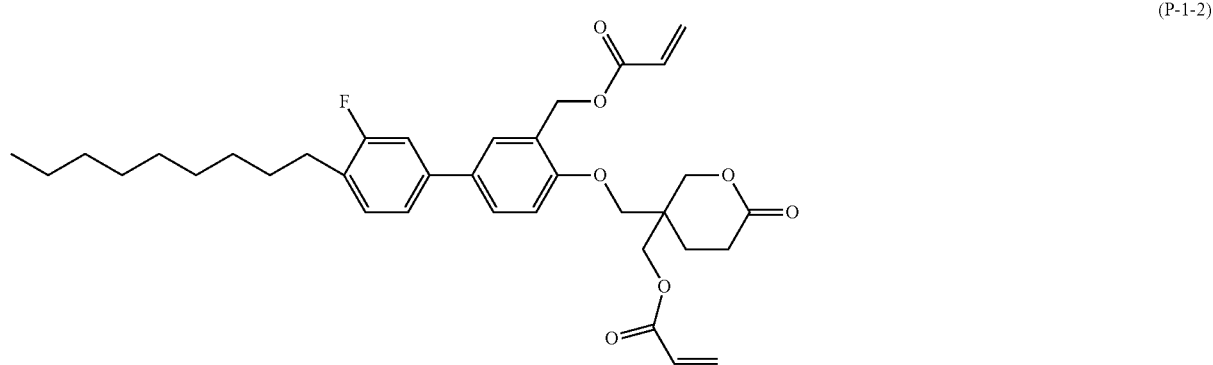
(P-1-2)

(P-1-3)
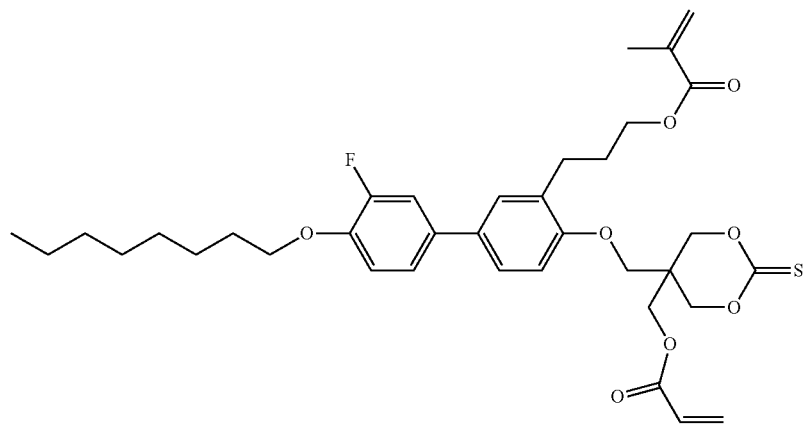
(P-1-4)
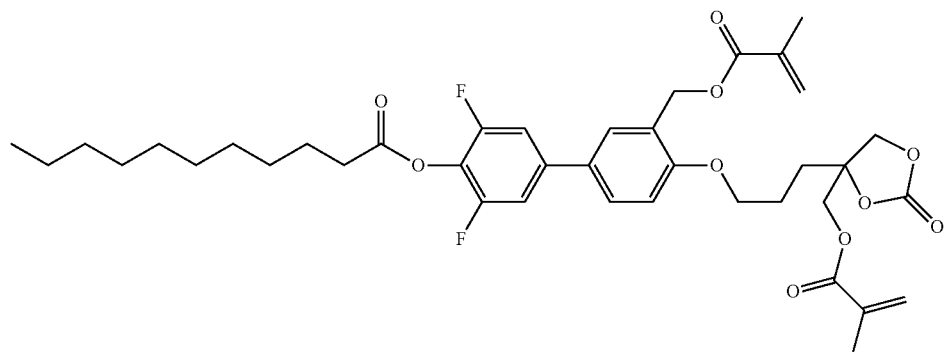
(P-1-5)
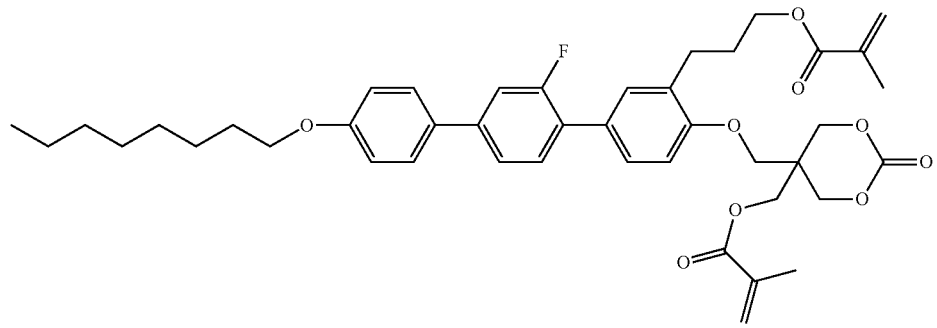
[Chem. 12]
(P-1-6)
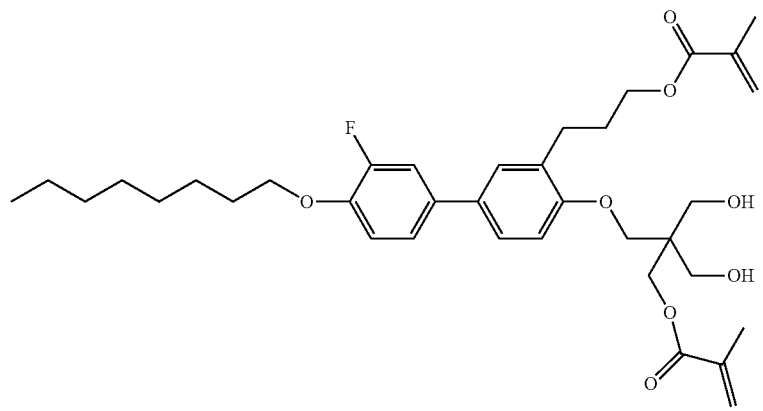

(P-1-7)
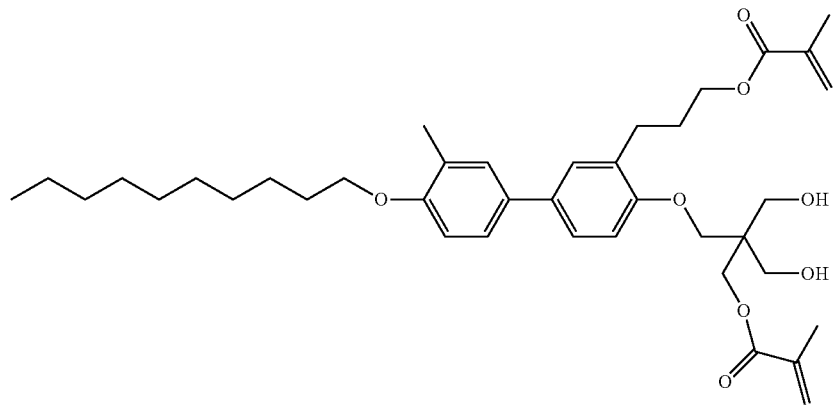
(P-1-8)
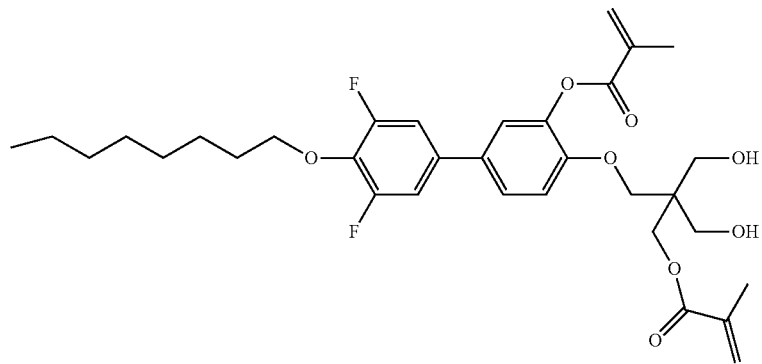
(P-1-9)
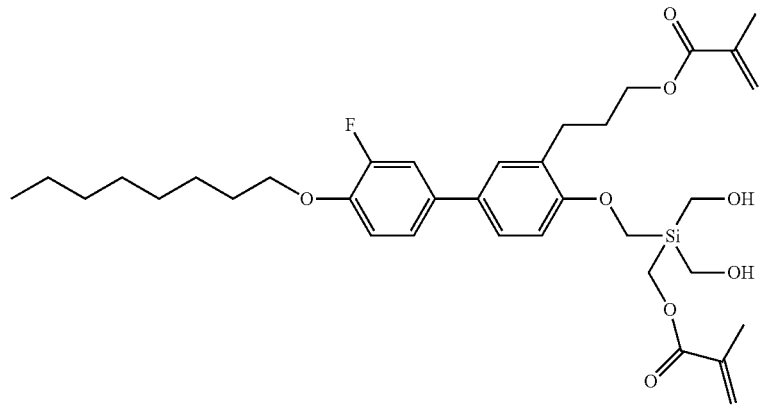
[Chem. 13]
(P-1-10)
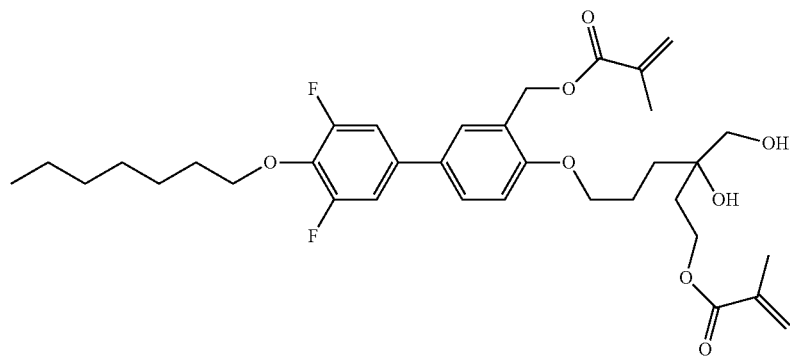

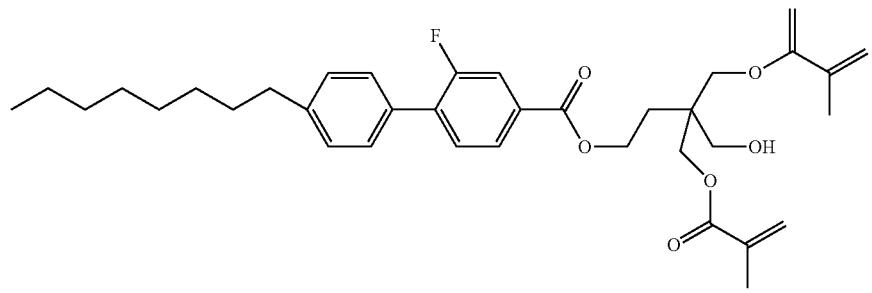
(P-1-11)
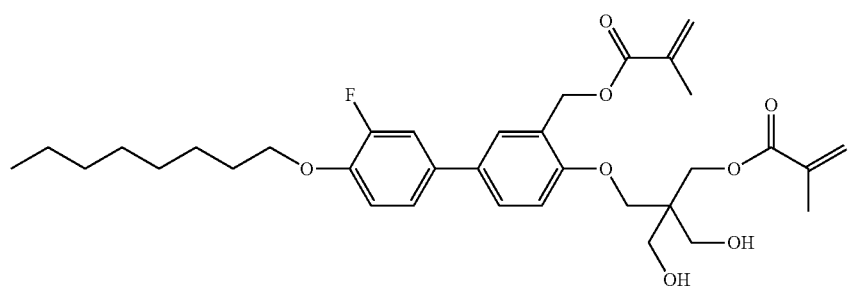
(P-1-12)
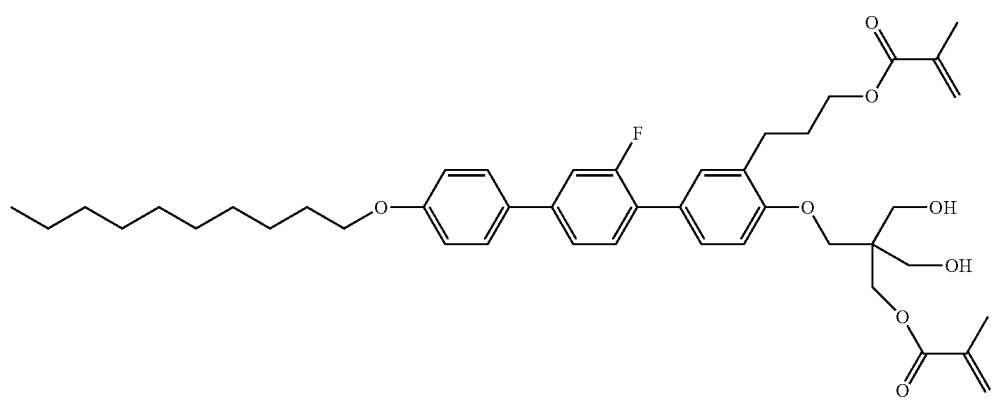
(P-1-13)
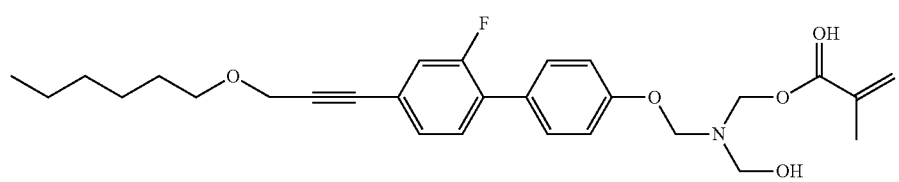
(R-1-14)
[Chem. 14]
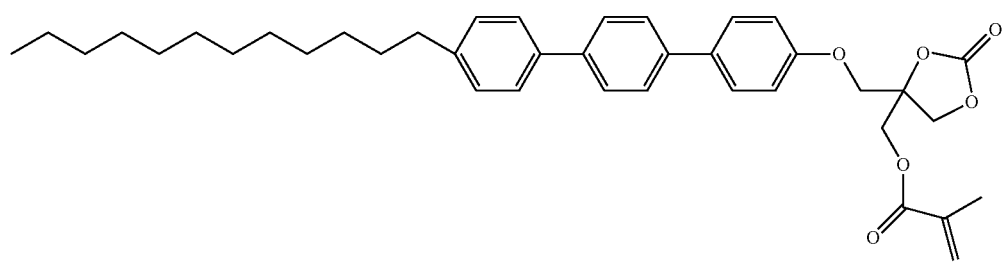
(P-1-15)

-continued
(P-1-16)
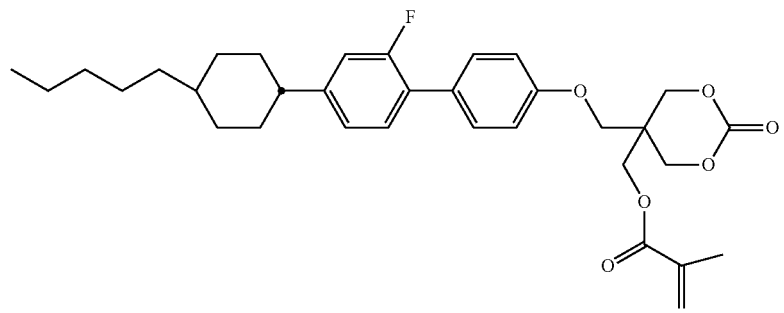
(P-1-17)
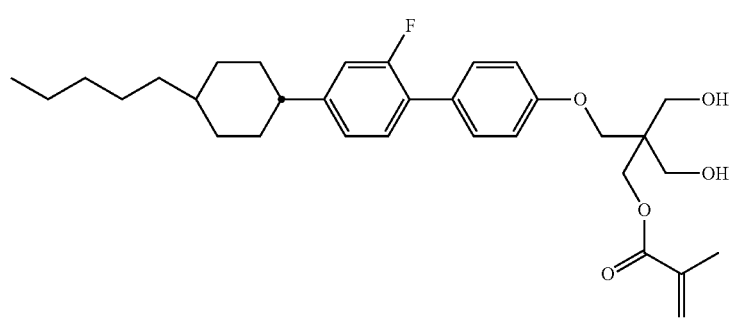
(P-1-18)
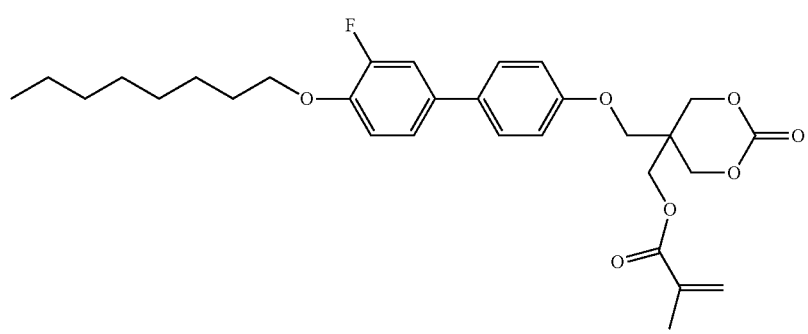
(R-1-19)
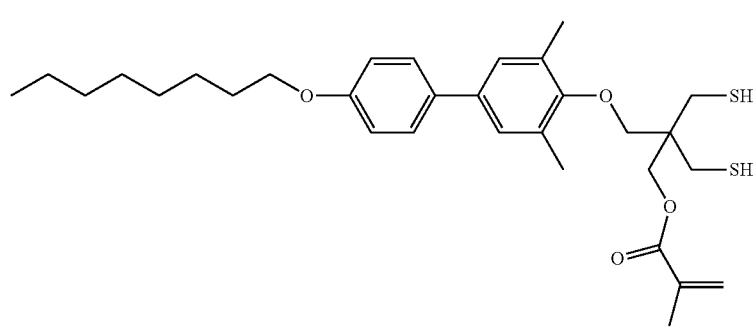

-continued
(P-1-20)
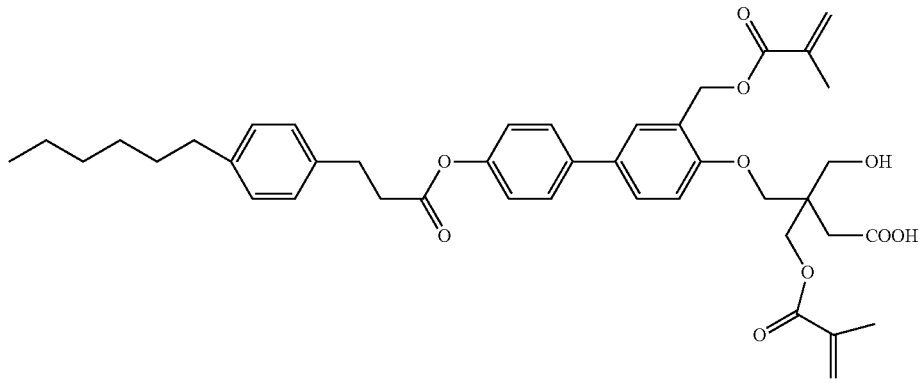
(P-1-21)
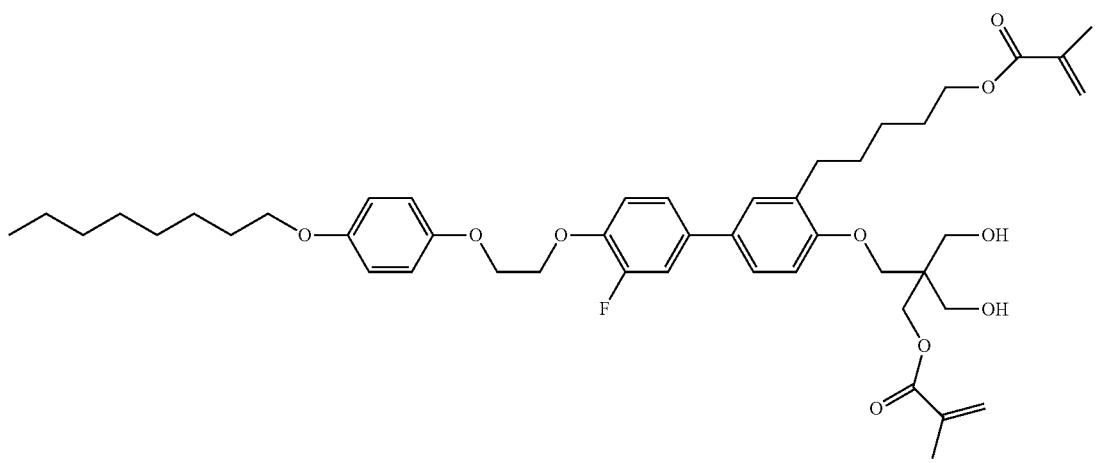
(P-1-22)
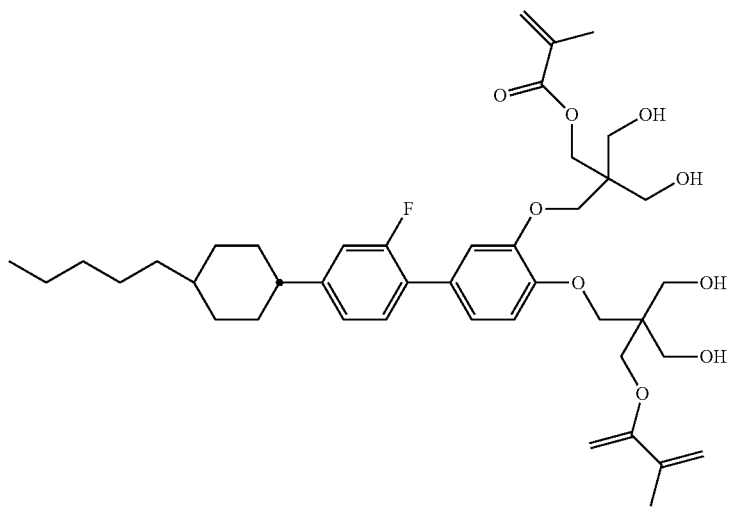
(P-1-23)
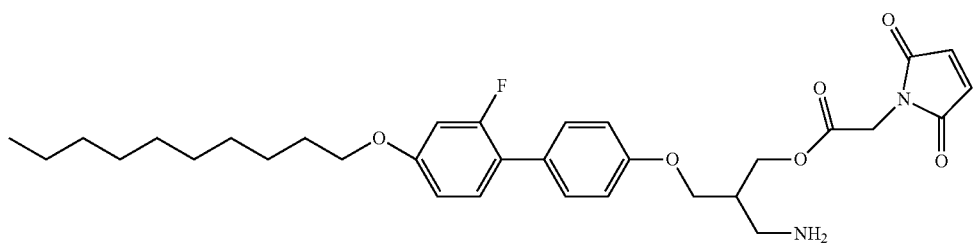

-continued
(P-1-24)
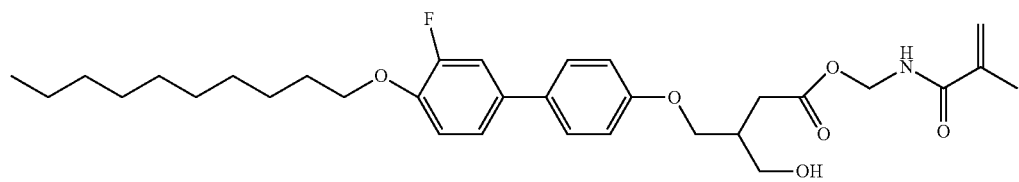
(P-1-25)
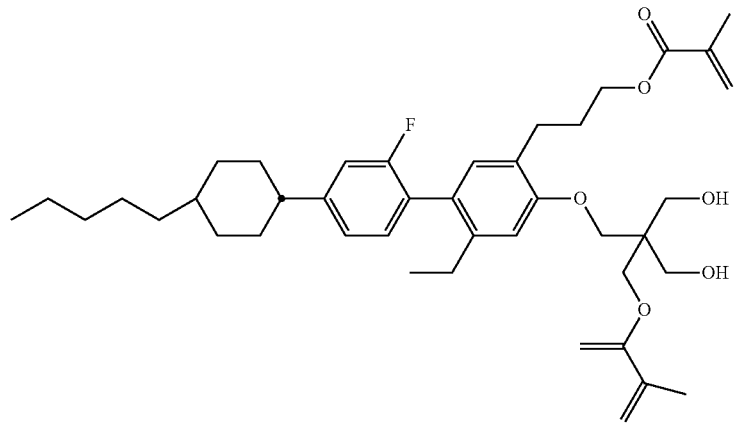
(P-1-26)
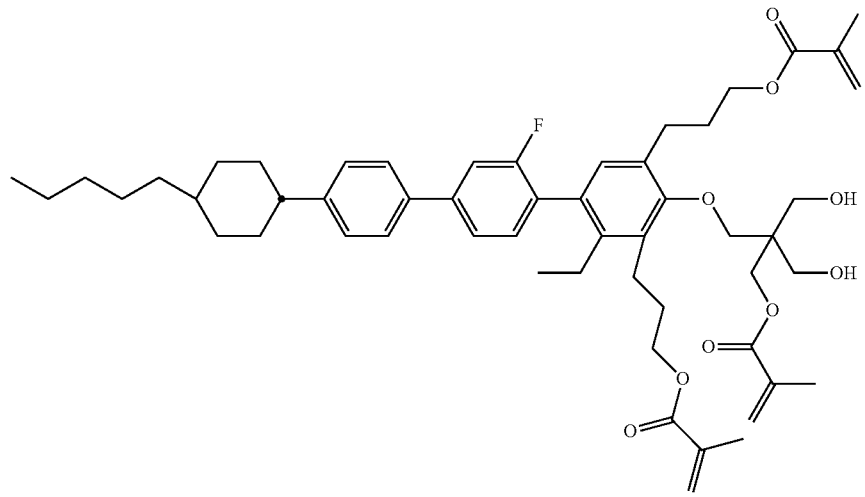
(P-1-27)
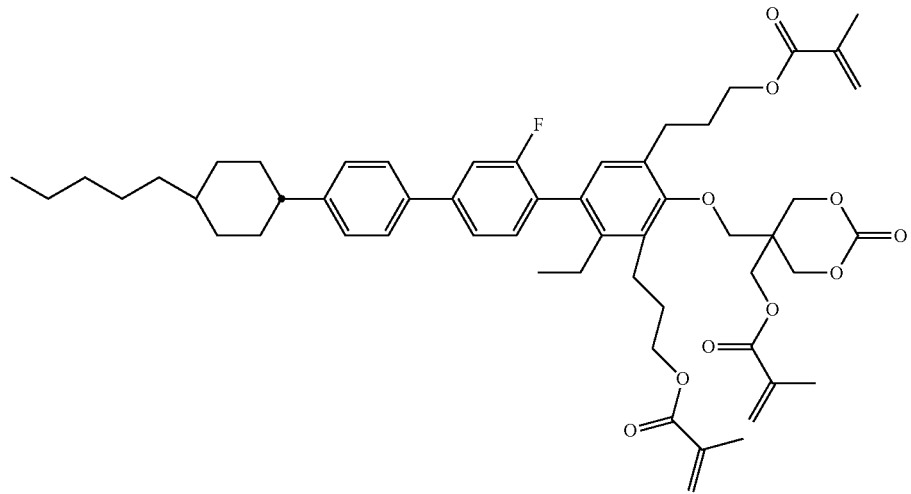

(Production Method 1) Method for Producing Compounds Represented by General Formulae (P-1-1) and (P-1-12)

(S-1) is produced by Suzuki Coupling reaction of 3-fluoro-4-(octyloxy)phenylboronic acid with 4-boromo-salicyl aldehyde using a palladium catalyst. Next, an alcohol derivative (S-3) is produced by etherification reaction with 5-(bromomethyl)-2,2-dimethyl-1,3-dioxan-5-yl) methanol and reduction reaction with sodium borohydride. Further, a diol compound (P-1-12) having a polymerizable group of the present invention is produced by esterification reaction with methacryl chloride and deketalization reaction with hydrochloric acid. Further, a target compound (P-1-1) can be produced by carbonation reaction with ethyl chloroformate.

[Chem. 16]

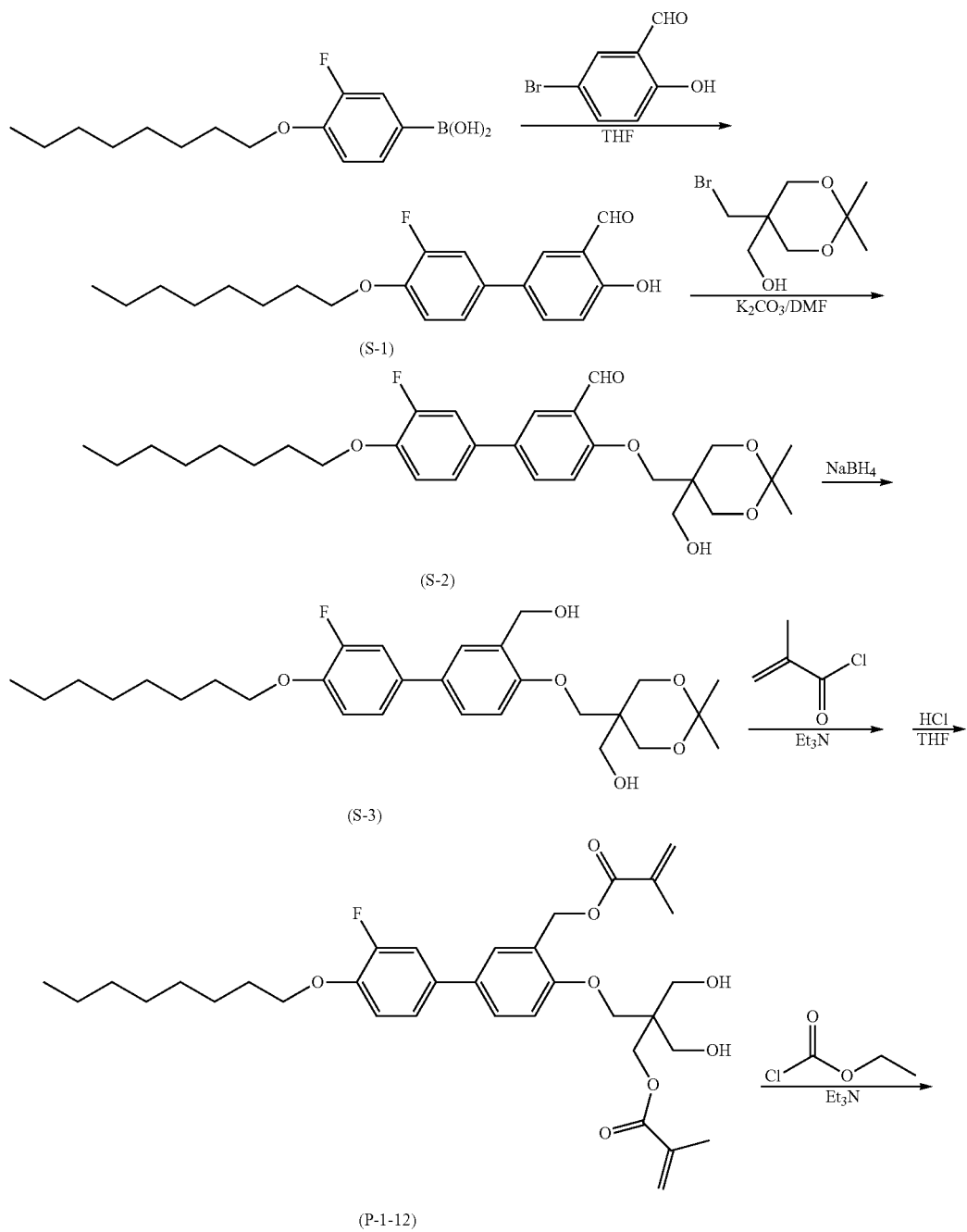

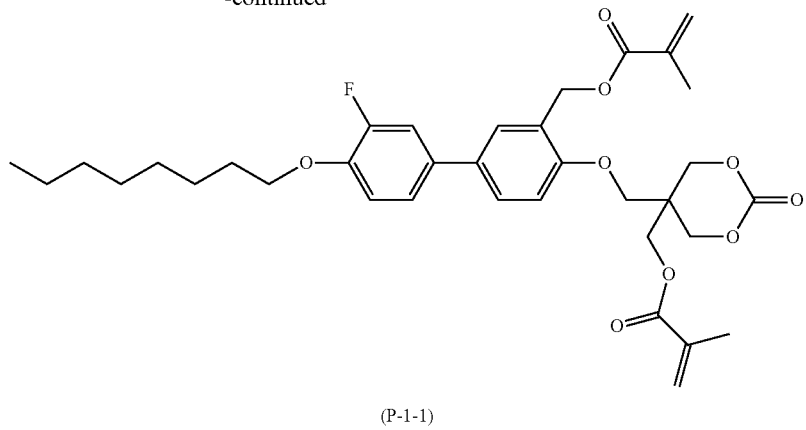

(P-1-1)

(Production Method 2) Production of Compound Represented by General Formula (P-1-5)

(S-4) is produced by Suzuki Coupling reaction of 4-(octyloxy)phenylboronic acid with 4-(4-bromo-2-fluoro)phenylphenol. Next, an alcohol derivative (S-5) is produced by bromination with bromine and etherification reaction with 5-(bromomethyl)-2,2-dimethyl-1,3-dioxan-5-yl) methanol.

Further, an alcohol derivative (S-6) is produced by Sonogashira reaction with propargyl alcohol. Next, a target compound (P-1-5) can be produced by esterification reaction with methacryl chloride, deketalization reaction with hydrochloric acid, and then carbonation reaction with ethyl chloroformate.

[Chem. 17]

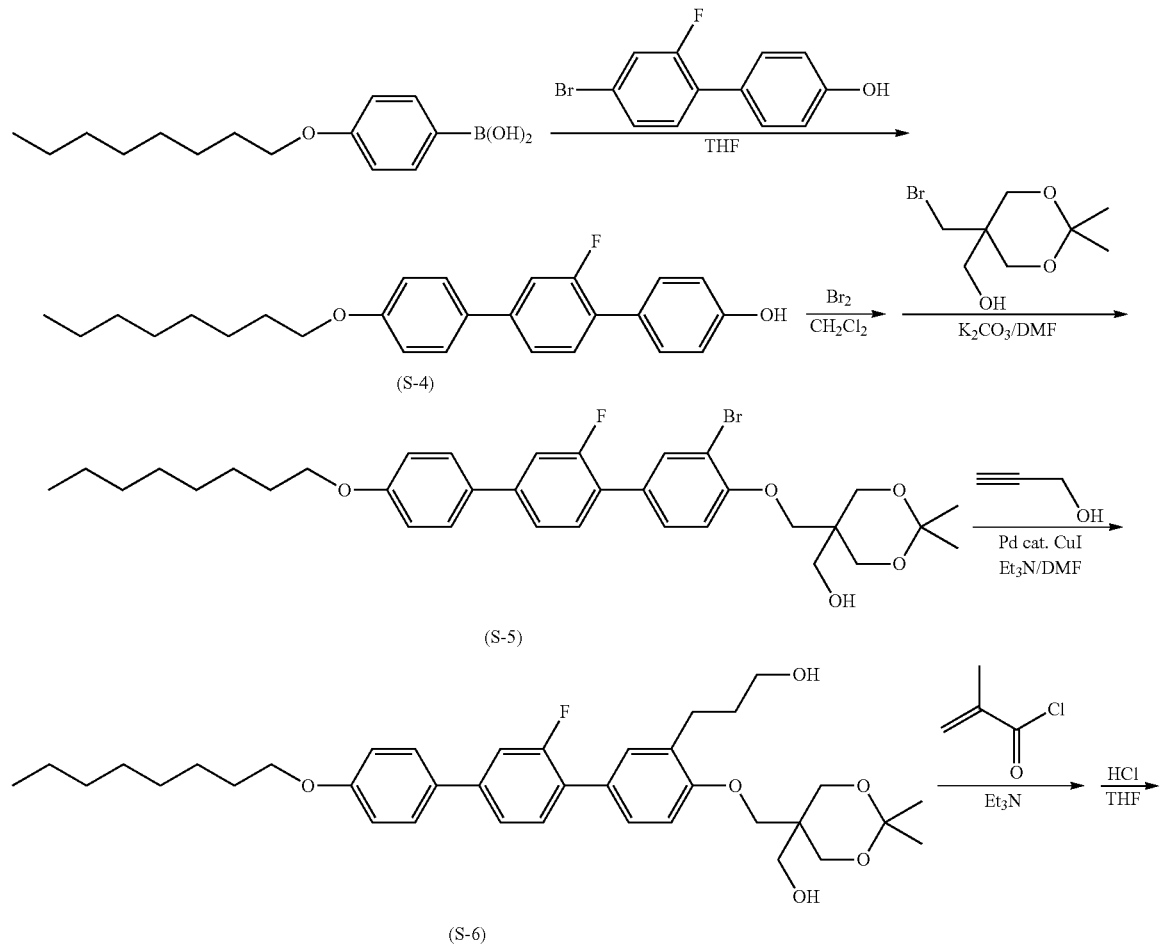

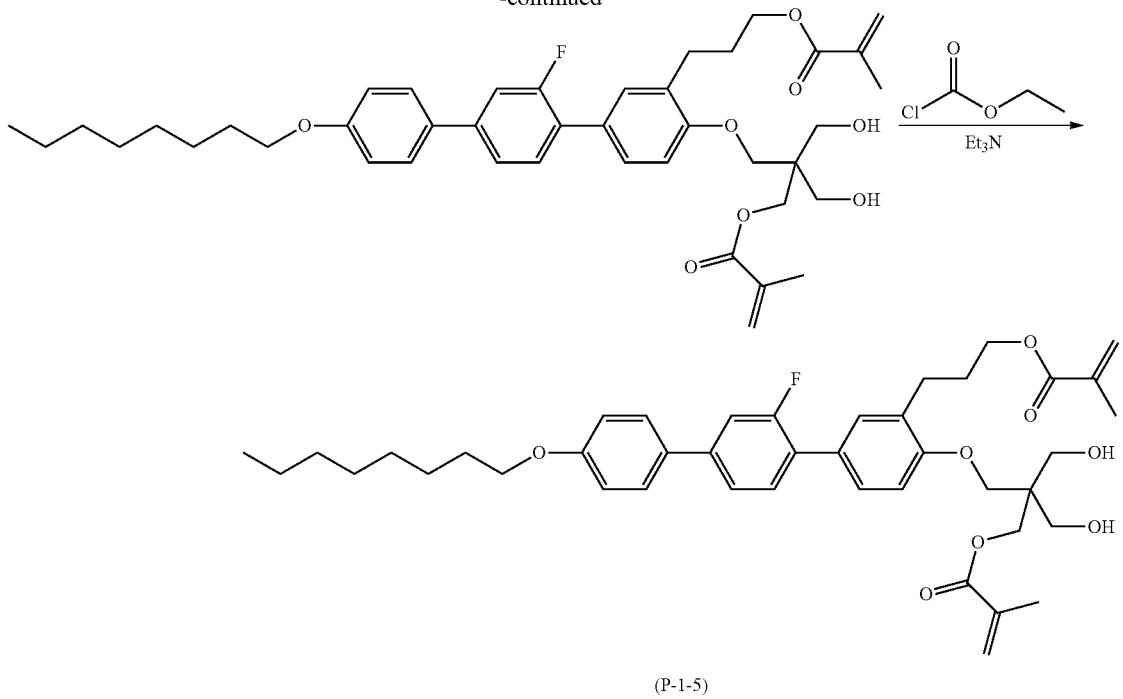

(P-1-5)

(Production Method 3) Production of Compound Represented by General Formula (P-1-6)

(S-7) is produced by Suzuki Coupling reaction of 3-fluoro-4-(octyloxy)phenylboronic acid with 4-bromophenol. Next, an alcohol derivative (S-8) is produced by bromination with bromine and etherification reaction with 5-(bromomethyl)-2,2-dimethyl-1,3-dioxan-5-yl) methanol. Further, an alcohol derivative (S-6) is produced by Sonogashira reaction with propargyl alcohol. Next, a target compound (P-1-6) can be produced by esterification reaction with methacryl chloride and then deketalization reaction with hydrochloric acid.

[Chem. 18]

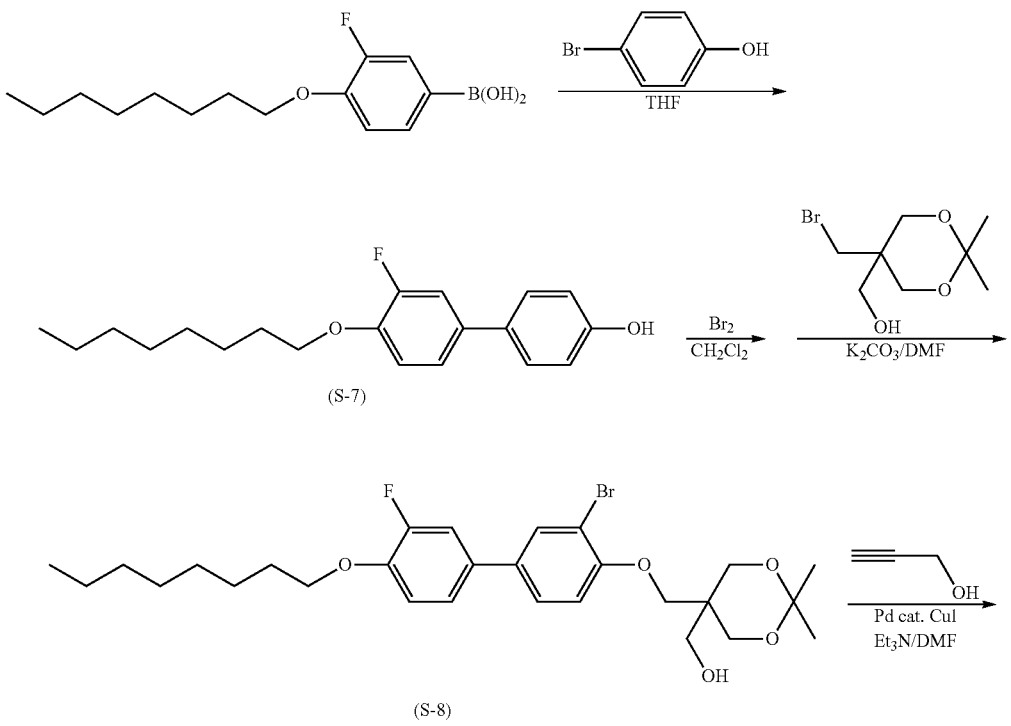

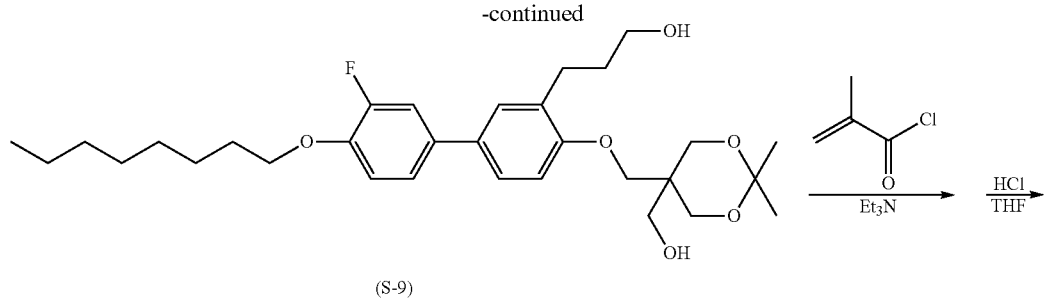

(S-9)

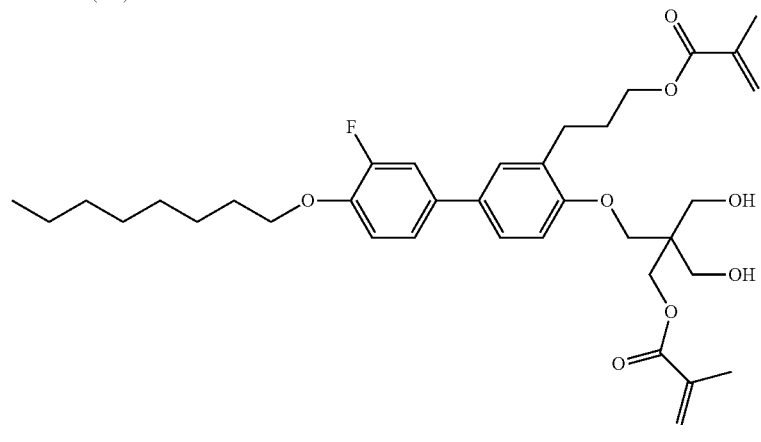

(P-1-6)

(Production Method 4) Production of Compound Represented by General Formula (P-1-9)

An alcohol derivative (S-10) is produced by etherification reaction of 3-bromo-4-(3'-fluoro-4'-(octyloxy)phenyl)phenol with (5-hydroxymethyl-2,2-dimethyl-1,3,5-dioxasilane-5-yl)methanesulfonic acid. Further, an alcohol derivative (S-11) is produced by Sonogashira reaction with propargyl alcohol. Next, a target compound (P-1-9) can be produced by esterification reaction with methacryl chloride and then deketalization reaction with hydrochloric acid.

[Chem. 19]

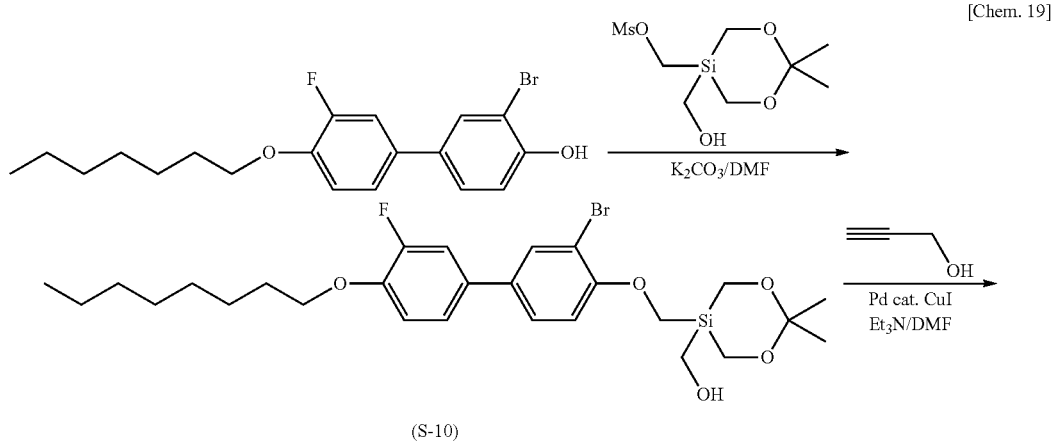

(S-10)

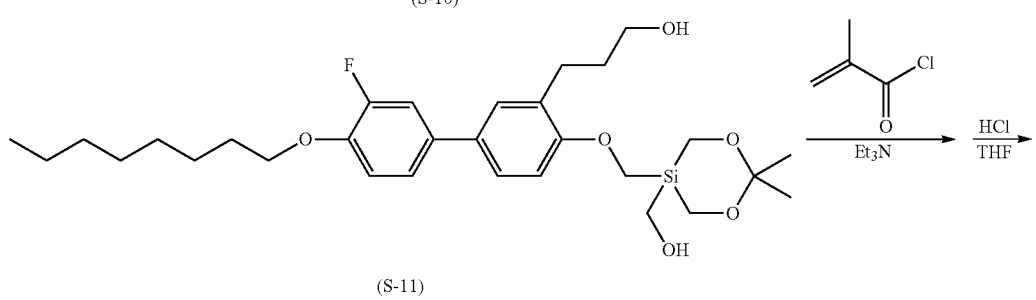

(S-11)

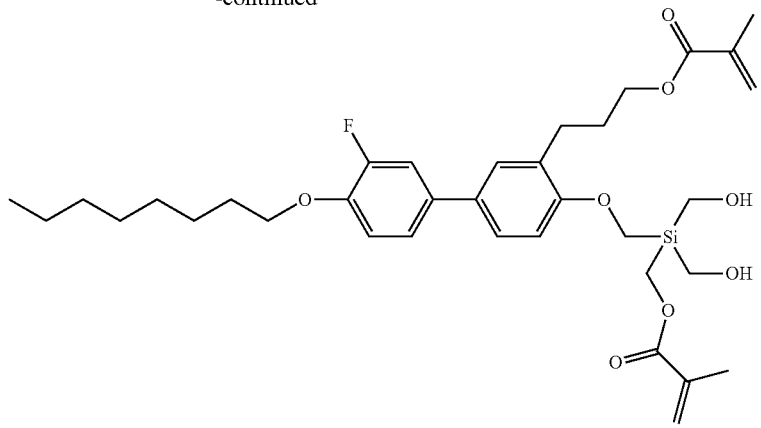

(P-1-9)

(Liquid Crystal Composition)

A liquid crystal composition according to an embodiment of the present invention contains one or two or more compounds represented by the general formula (i). The liquid crystal composition preferably has negative dielectric anisotropy ($\Delta\varepsilon$). The compounds represented by the general formula (i) and contained in the liquid crystal composition are the same as the compounds (i) described above including the compounds represented by the formulae (R-1-1) to (R-1-25), and thus the description thereof is omitted.

The content of a compound represented by the general formula (i) is preferably 0.01 to 50% by mass, and from the viewpoint of allowing liquid crystal molecules to be more preferably aligned, the lower limit value based on the total amount of the liquid crystal composition is preferably 0.01% by mass or more, 0.1% by mass or more, 0.5% by mass or more, 0.7% by mass or more, or 1% by mass or more. From the viewpoint of excellent response characteristics, the upper limit value of the content of the compound (i) based on the total amount of the liquid crystal composition is preferably 50% by mass or less, 30% by mass or less, 10% by mass or less, 7% by mass or less, 5% by mass or less, 4% by mass or less, or 3% by mass or less.

The liquid crystal composition may further contain a compound selected from a compound group represented by any one of general formulae (N-1), (N-2), and (N-3).

[Chem. 20]

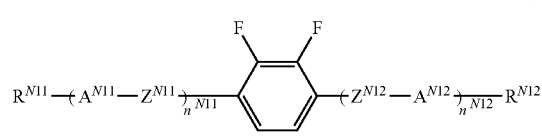
(N-1)

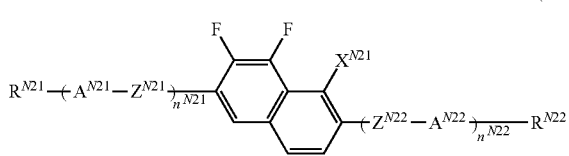
(N-2)

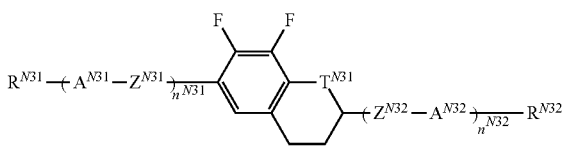
(N-3)

In the formulae (N-1), (N-2), and (N-3), $R^{N11}$, $R^{N12}$, $R^{N21}$, $R^{N22}$, $R^{N31}$, and $R^{N32}$ each independently represent an alkyl group having 1 to 8 carbon atoms, wherein one or two or more nonadjacent —$CH_2$— in the alkylene group may be each independently substituted by —CH=CH—, —C≡C—, —O—, —CO—, —COO—, or —OCO—;

$A^{N11}$, $A^{N12}$, $A^{N21}$, $A^{N22}$, $A^{N31}$, and $A^{N32}$ each independently represent a group selected from the group consisting of:

(a) a 1,4-cyclohexylene group (one —$CH_2$— or two or more nonadjacent —$CH_2$— in the group may be substituted by —O—);

(b) a 1,4-phenylene group (one —CH= or two or more nonadjacent —CH= in the group may be substituted by —N=);

(c) a naphthalene-2,6-diyl group, a 1,2,3,4-tetrahydronaphthalene-2,6-diyl group, or a decahydronaphthalene-2,6-diyl group (one —CH= or two or more nonadjacent —CH= in the naphthalene-2,6-diyl group or 1,2,3,4-tetrahydronaphthalene-2,6-diyl group may be substituted by —N=); and (d) a 1,4-cyclohexylene group.

The group (a), the group (b), the group (c), and the group (d) may be each independently substituted by a cyano group, a fluorine atom, a chlorine atom;

$Z^{N11}$, $Z^{N12}$, $Z^{N21}$, $Z^{N22}$, $Z^{N31}$, and $Z^{N32}$ each independently represent a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—;

$X^{N21}$ represents a hydrogen atom or a fluorine atom;

$T^{N31}$ represents —$CH_2$— or an oxygen atom;

$n^{N11}$, $n^{N12}$, $n^{N21}$, $n^{N22}$, $n^{N31}$, and $n^{N32}$ each independently represent an integer of 0 to 3, but $n^{N11}+n^{N12}$, $n^{N21}+n^{N22}$, and $n^{N31}+n^{N32}$ are each independently 1, 2, or 3; and when a plurality of each of $A^{N11}$ to $A^{N32}$ and $Z^{N11}$ to $Z^{N32}$ are present, they may be the same or different.

A compound represented by any one of the general formulae (N-1), (N-2), and (N-3) is preferably a compound having negative Δε and its absolute value of more than 3.

In the general formulae (N-1), (N-2), and (N-3), $R^{N11}$, $R^{N12}$, $R^{N21}$, $R^{N22}$, $R^{N31}$, and $R^{N32}$ are each independently an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, preferably an alkyl group having 1 to 5 carbon atoms, an alkoxy group having 1 to 5 carbon atoms, an alkenyl group having 2 to 5 carbon atoms, or an alkenyloxy group having 2 to 5 carbon atoms, more preferably an alkyl group having 1 to 5 carbon atoms or an alkenyl group having 2 to 5 carbon atoms, still more preferably an alkyl group having 2 to 5 carbon atoms or an alkenyl group having 2 to 3 carbon atoms, and particularly preferably an alkenyl group (propenyl group) having 3 carbon atoms.

When the cyclic structure bonded is a phenyl group (aromatic), a linear alkyl group having 1 to 5 carbon atoms, a linear alkoxy group having 1 to 4 carbon atoms, or an alkenyl group having 4 to 5 carbon atoms is preferred, while when the cyclic structure is a saturated cyclic structure such as cyclohexane, pyran, or dioxane, a linear alkyl group having 1 to 5 carbon atoms, a linear alkoxy group having 1 to 4 carbon atoms, or a linear alkenyl group having 2 to 5 carbon atoms is preferred. In order to stabilize a nematic phase, the total number of carbon atoms and, when present, oxygen atoms is preferably 5 or more, and a linear group is preferred.

An alkenyl group is preferably selected from groups represented by any one of formula ($R^1$) to formula ($R^5$) (in each of the formulae, a black point represents a bond).

[Chem. 21]

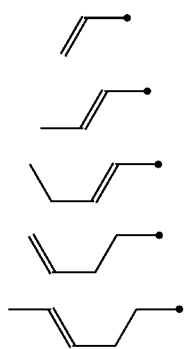

(R1)
(R2)
(R3)
(R4)
(R5)

When Δn is required to be increased, $A^{N11}$, $A^{N12}$, $A^{N21}$, $A^{N22}$, $A^{N31}$, and $A^{N32}$ are preferably each independently aromatic, and in order to improve the response speed, an aliphatic is preferred. $A^{N11}$, $A^{N12}$, $A^{N21}$, $A^{N22}$, $A^{N31}$, and $A^{N32}$ preferably each independently represent a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperizine-1,4-diyl group, a naphthalene-2,6-diyl group, a decahydronaphthalene-2,6-diyl group, or a 1,2,3,4-tetrahydronaphthalene-2,6-diyl group, more preferably represent the following structure, and

[Chem. 22]

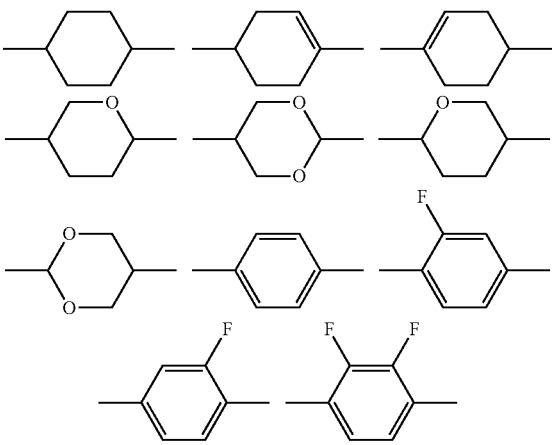

more preferably represent a trans-1,4-cyclohexylene group, a 1,4-cyclohexenylene group, or a 1,4-phenylene group.

$Z^{N11}$, $Z^{N12}$, $Z^{N21}$, $Z^{N22}$, $Z^{N31}$, and $Z^{N32}$ preferably each independently represent $-CH_2O-$, $-CF_2O-$, $-CH_2CH_2-$, $-CF_2CF_2-$, or a single bond, more preferably each independently represent $-CH_2O-$, $-CH_2CH_2-$, or a single bond, and particularly preferably each independently represent $-CH_2O-$ or a single bond.

$X^{N21}$ is preferably a fluorine atom.

$T^{N31}$ is preferably an oxygen atom.

$n^{N11}+n^{N12}$, $n^{N21}+n^{N22}$, and $n^{N31}+n^{N32}$ are preferably each 1 or 2, and preferred are a combination of $n^{N11}$ of 1 and $n^{N12}$ of 0, a combination of $n^{N11}$ of 2 and $n^{N12}$ of 0, a combination of $n^{N11}$ of 1 and $n^{N12}$ of 1, a combination of $n^{N11}$ of 2 and $n^{N12}$ of 1, a combination of $n^{N21}$ of 1 and $n^{N22}$ of 0, a combination of $n^{N21}$ of 2 and $n^{N22}$ of 0, a combination of $n^{N31}$ of 1 and $n^{N32}$ of 0, and a combination of $n^{N31}$ of 2 and $n^{N32}$ of 0.

The lower limit value of the preferred content of a compound represented by the formula (N-1) relative to the total amount of the composition according to the embodiment is 1% by mass or more, 10% by mass or more, 20% by mass or more, 30% by mass or more, 40% by mass or more, 50% by mass or more, 55% by mass or more, 60% by mass or more, 65% by mass or more, 70% by mass or more, or 75% by mass or more, 80% by mass or more. The upper limit value of the preferred content is 95% by mass or less, 85% by mass or less, 75% by mass or less, 65% by mass or less, 55% by mass or less, 45% by mass or less, 35% by mass or less, 25% by mass or less, or 20% by mass or less.

The lower limit value of the preferred content of a compound represented by the formula (N-2) relative to the total amount of the composition according to the embodiment is 1% by mass or more, 10% by mass or more, 20% by mass or more, 30% by mass or more, 40% by mass or more, 50% by mass or more, 55% by mass or more, 60% by mass or more, 65% by mass or more, 70% by mass or more, 75% by mass or more, or 80% by mass or more. The upper limit value of the preferred content is 95% by mass or less, 85% by mass or less, 75% by mass or less, 65% by mass or less, 55% by mass or less, 45% by mass or less, 35% by mass or less, 25% by mass or less, or 20% by mass or less.

The lower limit value of the preferred content of a compound represented by the formula (N-3) relative to the total amount of the composition according to the embodiment is 1% by mass or more, 10% by mass or more, 20% by mass or more, 30% by mass or more, 40% by mass or more, 50% by mass or more, 55% by mass or more, 60% by mass or more, 65% by mass or more, 70% by mass or more, 75% by mass or more, or 80% by mass or more. The upper limit value of the preferred content is 95% by mass or less, 85% by mass or less, 75% by mass or less, 65% by mass or less, 55% by mass or less, 45% by mass or less, 35% by mass or less, 25% by mass or less, or 20% by mass or less.

When the viscosity of the composition according to the embodiment is kept low, and the composition having a high response speed is required, preferably, the lower limit value is low, and the upper limit value is low. Further, when Tni of the composition according to the embodiment is kept high, and the composition having good temperature stability is required, preferably, the lower limit value is low, and the upper limit value is low. In addition, when dielectric anisotropy is desired to be increased for keeping the drive voltage low, preferably, the lower limit value is high, and the upper limit value is high.

Examples of the compound represented by the general formula (N-1) include a compound group represented by general formulae (N-1a) to (N-1g) below.

[Chem. 23]

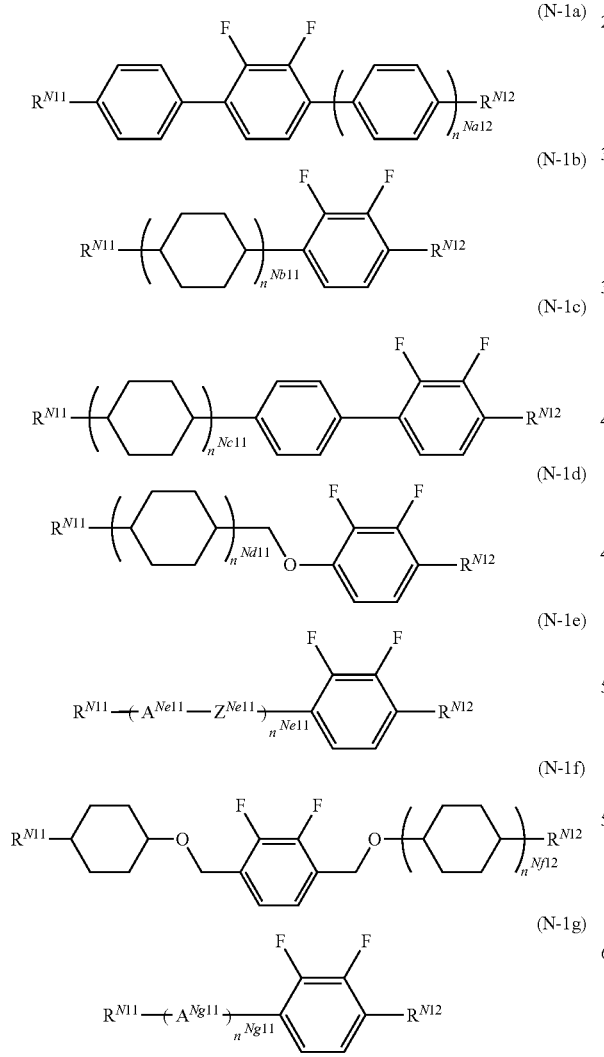

(In the formulae, $R^{N11}$ and $R^{N12}$ represents the same meanings as $R^{N11}$ and $R^{N12}$, respectively, in the general formula (N-1); $n^{Na11}$ represents 0 or 1, $n^{Nb11}$ represents 0 or 1, $n^{Nc11}$ represents 0 or 1, $n^{Nd11}$ represents 0 or 1, $n^{Ne11}$ represents 1 or 2, $n^{Nf11}$ represents 1 or 2, and $n^{Ng11}$ represents 1 or 2; $A^{Ne11}$ represents a trans-1,4-cyclohexylene group or a 1,4-phenylene group, $A^{Ng11}$ represents a trans-1,4-cyclohexylene group, a 1,4-cyclohexenylene group, or a 1,4-phenylene group, and at least one represents a 1,4-cyclohexenylene group; and $Z^{Ne11}$ represents a single bond or an ethylene group, and at least one represents an ethylene group.) More specifically, the compound represented by the general formula (N-1) is preferably a compound selected from a compound group represented by general formulae (N-1-1) to (N-1-21).

A compound represented by the general formula (N-1-1) is the following compound.

[Chem. 24]

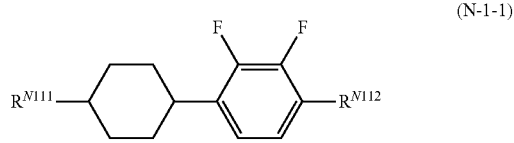

(In the formula, $R^{N111}$ and $R^{N112}$ represent the same meanings as $R^{N11}$ and $R^{N12}$, respectively, in the general formula (N).)

$R^{N111}$ is preferably an alkyl group having 1 to 5 carbon atoms or an alkenyl group having 2 to 5 carbon atoms, and preferably a propyl group, a pentyl group, or a vinyl group. $R^{N112}$ is preferably an alkyl group having 1 to 5 carbon atoms, an alkenyl group having 4 to 5 carbon atoms, or an alkoxy group having 1 to 4 carbon atoms, and preferably an ethoxy group or a butoxy group.

Compounds represented by the general formula (N-1-1) can be used alone or in combination of two or more. The types of compounds which can be combined is not particularly limited, but the compounds are used in proper combination according to the desired performance such as solubility at low temperature, the transition temperature, electric reliability, birefringence etc. For example, in an embodiment, the number of types of the compounds used is 1, 2, 3, 4, or 5 or more.

When improvement in Δε is regarded as important, the content is preferably set to be relatively high, when solubility at low temperature is regarded as important, a high effect can be obtained by setting the content to be relatively high, and when $T_{NI}$ is regarded as important, a high effect can be obtained by setting the content to be relatively low. Further, when drop marks and image-sticking characteristics are improved, the content is preferably set within a middle range.

The lower limit value of the preferred content of a compound represented by the formula (N-1-1) relative to the total amount of the liquid crystal composition according to the embodiment is 5% by mass or more, 10% by mass or more, 13% by mass or more, 15% by mass or more, 17% by mass or more, 20% by mass or more, 23% by mass or more, 25% by mass or more, 27% by mass or more, 30% by mass or more, 33% by mass or more, or 35% by mass or more. The upper limit value of the preferred content relative to the total amount of the composition according to the embodiment is 50% by mass or less, 40% by mass or less, 38% by mass or less, 35% by mass or less, 33% by mass or less, 30% by mass or less, 28% by mass or less, 25% by mass or less, 23% by mass or less, 20% by mass or less, 18% by mass or less, 15% by mass or less, 13% by mass or less, 10% by mass or less, 8% by mass or less, 7% by mass or less, 6% by mass or less, 5% by mass or less, or 3% by mass or less.

Further, the compound represented by the general formula (N-1-1) is preferably a compound selected from a compound group represented by formula (N-1-1.1) to formula (N-1-1.23), preferably a compound represented by any one of the formulae (N-1-1.1) to (N-1-1.4), and preferably a compound represented by the formula (N-1-1.1) and the formula (N-1-1.3).

[Chem. 25]

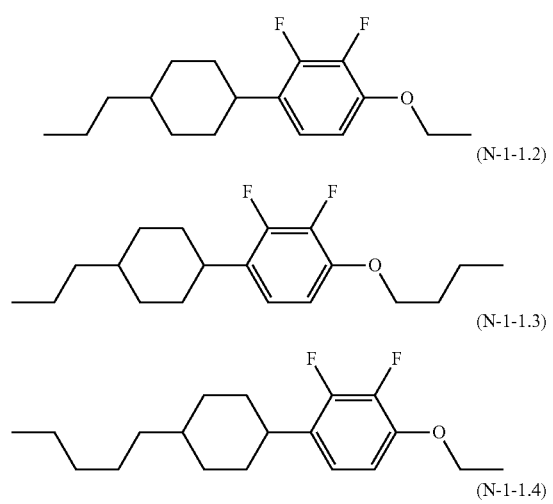

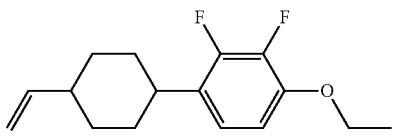
(N-1-1.20)

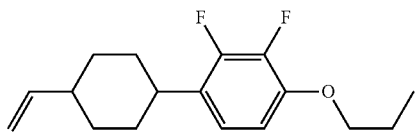
(N-1-1.21)

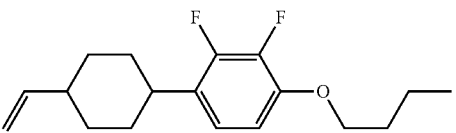
(N-1-1.22)

The compounds represented by the formulae (N-1-1.1) to (N-1-1.22) can be used alone or in combination, and the lower limit value of the preferred content of one or more of these compounds relative to the total amount of the composition according to the embodiment is 5% by mass or more, and the upper limit value relative to the total amount of the composition according to the embodiment is 50% by mass or less.

The liquid crystal composition of the present invention may further contain a polymerizable compound. The polymerizable compound may be a known polymerizable compound used for a liquid crystal composition. Examples of the polymerizable compound include compounds represented by general formula (P):

[Chem. 26]

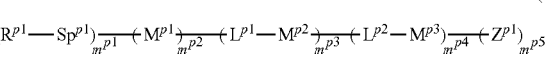
(P)

In the formula (P), $Z^{p1}$ represents a fluorine atom, a cyano group, a hydrogen atom, an alkyl group having 1 to 15 carbon atoms, in which a hydrogen atom may be substituted by a halogen atom, an alkoxy group having 1 to 15 carbon atoms, in which a hydrogen atom may be substituted by a halogen atom, an alkenyl group having 1 to 15 carbon atoms, in which a hydrogen atom may be substituted by a halogen atom, an alkenyloxy group having 1 to 15 carbon atoms, in which a hydrogen atom may be substituted by a halogen atom, or -Sp$^{p2}$—R$^{p2}$.

R$^{p1}$ and R$^{p2}$ each represent any one of the following formula (R—I) to formula (R-VIII):

[Chem. 27]

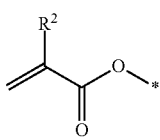
(R-I)

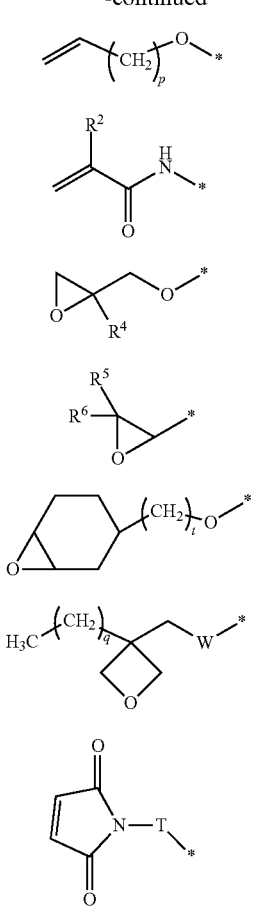

(R-II)
(R-III)
(R-IV)
(R-V)
(R-VI)
(R-VII)
(R-VIII)

(in the formulae,
* represents a bond to Sp$^{p1}$;
$R^2$ to $R^6$ each independently represent a hydrogen atom, an alkyl group having 1 to 5 carbon atoms, or an alkyl halide group having 1 to 5 carbon atoms;
W represents a single bond, —O—, or a methylene group;
T represents a single bond or —COO—; and
p, t, and q each independently represent 0, 1, or 2).
Sp$^{p1}$ and Sp$^{p2}$ each represent a pacer group;
L$^{p1}$ and L$^{p2}$ each independently represent a single bond, —O—, —S—, —CH$_2$—, —OCH$_2$—, —CH$_2$O—, —CO—, —C$_2$H$_4$—, —COO—, —OCO—, —OCOOCH$_2$—, —CH$_2$OCOO—, —OCH$_2$CH$_2$O—, —CO—NR$^a$—, —NR$^a$—CO—, —SCH$_2$—, —CH$_2$S—, —CH=CR$^a$—COO—, —CH=CR$^a$—OCO—, —COO—CR$^a$=CH—, —OCO—CR$^a$=CH—, —COO—CR$^a$=CH—COO—, —COO—CR$^a$=CH—OCO—, —OCO—CR$^a$=CH—COO—, —OCO—CR$^a$=CH—OCO—, —(CH$_2$)$_z$—C(=O)—O—, —(CH$_2$)$_z$—O—(C=O)—, —O—(C=O)—(CH$_2$)$_z$—, —(C=O)—O—(CH$_2$)$_z$—, —CH=CH—, —CF=CF—, —CF=CH—, —CH=CF—, —CF$_2$—, —CF$_2$O—, —OCF$_2$—, —CF$_2$CH$_2$—, —CH$_2$CF$_2$—, —CF$_2$CF$_2$—, or —C≡C— (wherein R$^a$ each independently represent a hydrogen atom or an alkyl group having 1 to 4 carbon atoms, and z represents an integer of 1 to 4);
M$^{p2}$ represents a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indane-2,5-diyl group, a 1,2,3,4-tetrehydronaphthalene-2,6-diyl group, a 1,3-dioxane-2,5-diyl group, or a single bond, and M$^{p2}$ is may be unsubstituted or substituted by an alkyl group having 1 to 12 carbon atoms, an alkyl halide group having 1 to 12 carbon atoms, an alkoxy group having 1 to 12 carbon atoms, an alkoxy halide group having 1 to 12 carbon atoms, a halogen atom, a cyano group, a nitro group, or —R$^{p1}$;
M$^{p1}$ represents any one of the following formulae (i-11) to (ix-11):

[Chem. 28]

(i-11)
(iv-11)
(vii-11)
(ii-11)
(v-11)
(viii-11)
(iii-11)
(vi-11)
(ix-11)

(in the formulae, * represents a bond to Sp$^{p1}$, and ** represents a bond to L$^{p1}$, L$^{p2}$, or Z$^{p1}$);

a hydrogen atom of $M^{p1}$ is may be substituted by an alkyl group having 1 to 12 carbon atoms, an alkyl halide group having 1 to 12 carbon atoms, an alkoxy group having 1 to 12 carbon atoms, an alkoxy halide group having 1 to 12 carbon atoms, a halogen atom, a cyano group, a nitro group, or —$R^{p1}$;

$M^{p3}$ represents any one of the following formulae (i-13) to (ix-13):

[Chem. 29]

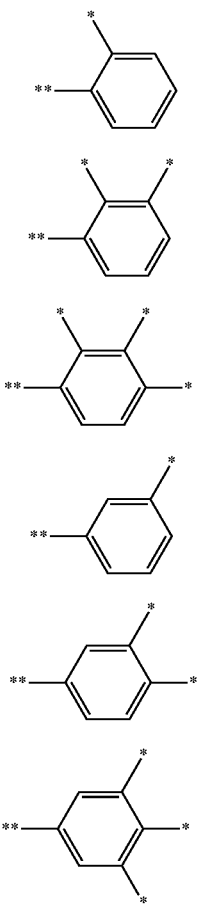

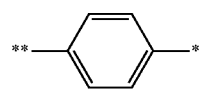

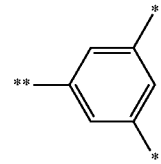

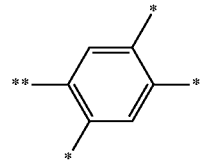

(in the formulae, * represents a bond to $Zp^{p1}$, and ** represents a bond to $L^{p2}$);

a hydrogen atom of $M^{p3}$ is may be substituted by an alkyl group having 1 to 12 carbon atoms, an alkyl halide group having 1 to 12 carbon atoms, an alkoxy group having 1 to 12 carbon atoms, an alkoxy halide group having 1 to 12 carbon atoms, a halogen atom, a cyano group, a nitro group, or —$R^{p1}$;

$m^{p2}$ to $m^{p4}$ each independently represent 0, 1, 2, or 3;

$m^{p1}$ and $m^{p5}$ each independently represent 1, 2, or 3;

when a plurality of $Z^{p1}$ are present, they may be the same or different; when a plurality of $R^{p1}$ are present, they may be the same or different; when a plurality of $Rp^{p2}$ are present, they may be the same or different; when a plurality of $Sp^{p1}$ are present, they may be the same or different; when a plurality of $Sp^{p2}$ are present, they may be the same or different; when a plurality of $L^{p1}$ are present, they may be the same or different; and when a plurality of $M^{p2}$ are present, they may be the same or different.

When the liquid crystal composition according to the embodiment further contains the polymerizable compound (P) represented by the general formula (P) in addition to the compound (i), the pretilt angle of liquid crystal molecules can be preferably formed. Specific examples of the polymerizable compound represented by the general formula (P) are represented by (P-2-1) to (P-2-20).

[Chem. 30]

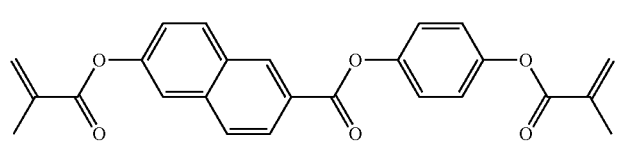

(P-2-1)

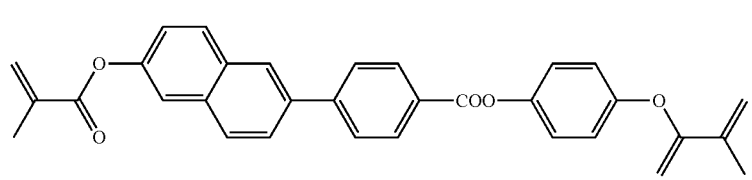

(P-2-2)

(P-2-3)
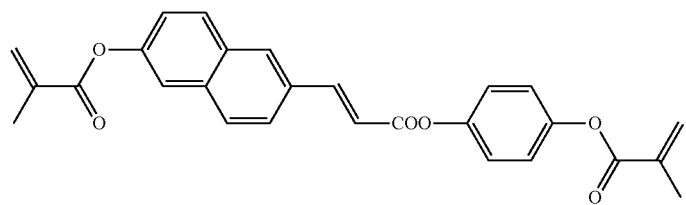
(P-2-4)
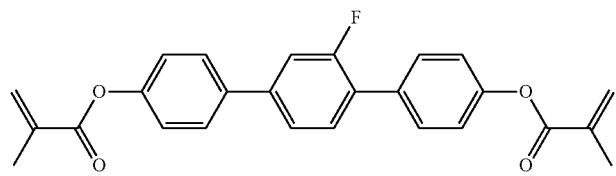
(P-2-5)
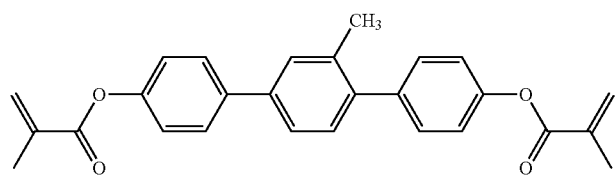
(P-2-6)
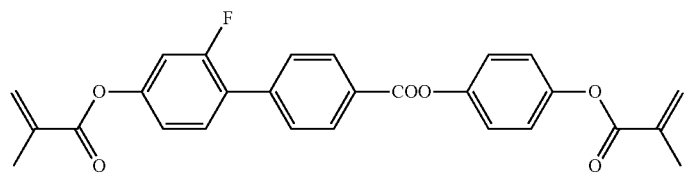
(P-2-7)
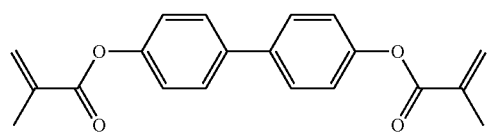
(P-2-8)
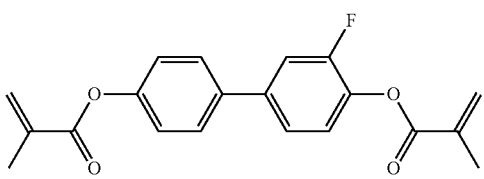
(P-2-9)
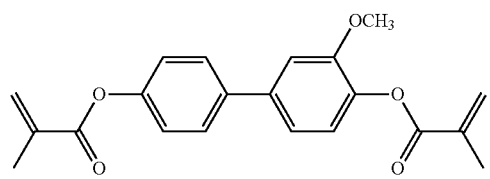
(P-2-10)
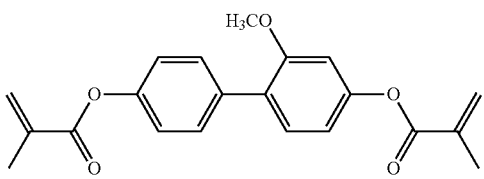
(P-2-11)
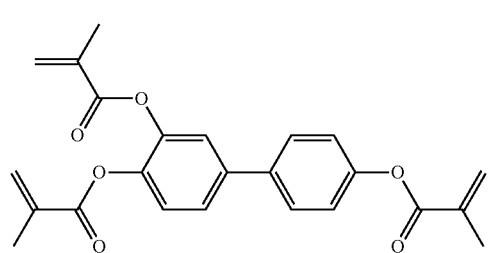
[Chem. 31]
(P-2-12)
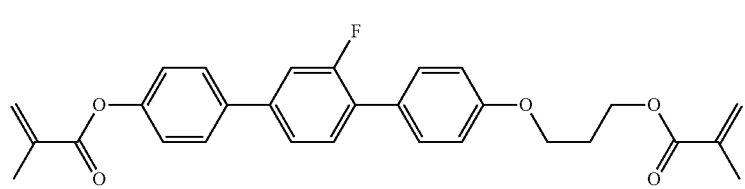

-continued (P-2-13)
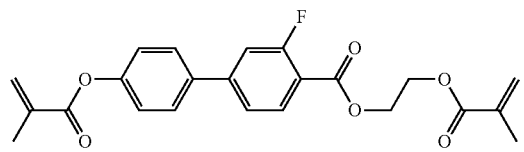

(P-2-14)
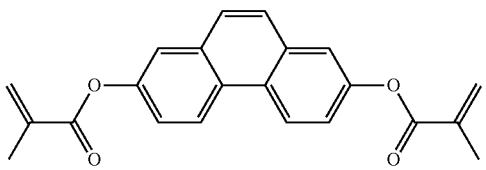

(P-2-15)
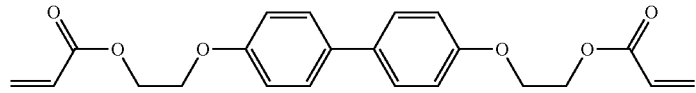

(P-2-16)
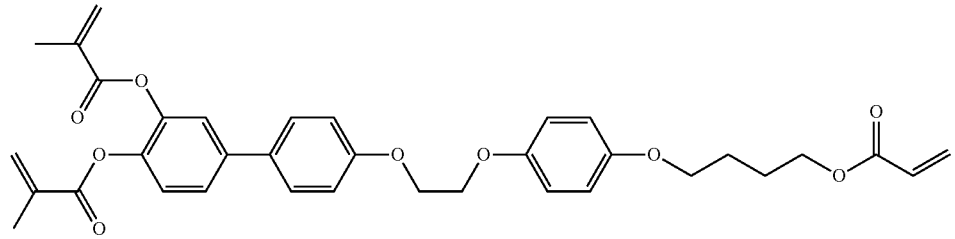

(P-2-17)
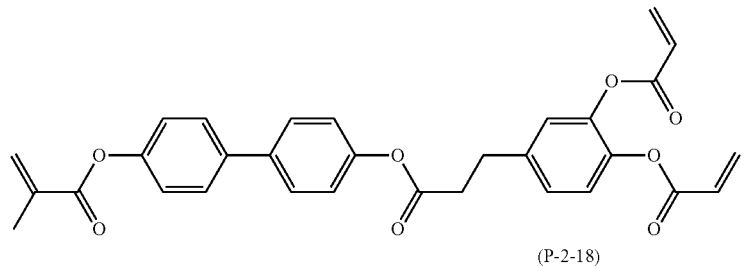

(P-2-18)
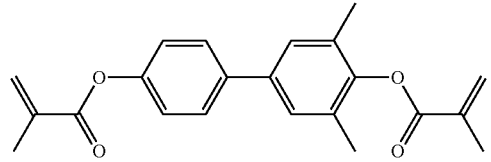

(P-2-19)
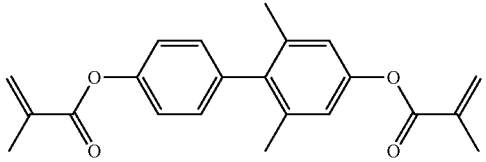

(P-2-20)
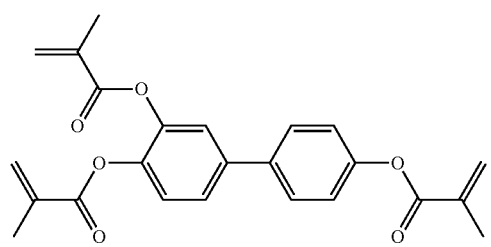

Also, besides the compound represented by the general formula (i), the liquid crystal composition of the present invention may further contain a known self-alignment aid for a liquid crystal composition.

(Liquid Crystal Display Device)

The liquid crystal composition according to the embodiment is applied to a liquid crystal display device. The liquid crystal display device may be a liquid crystal display device for active matrix driving. The liquid crystal display device 1 may be a PSA-mode, PSVA-mode, VA-mode, IPS-mode, FFS-mode, or ECB-mode liquid crystal display device, and is preferably a PSA-mode liquid crystal display device.

A liquid crystal display device according to an embodiment of the present invention uses the liquid crystal composition containing the compound represented by the general formula (i), and thus an alignment film such as a polyimide alignment film or the like need not be provided on the liquid crystal layer side of each of a first substrate and a second substrate. That is, the liquid crystal display device according to the embodiment can take a configuration in which at least one of the two substrates does not have an alignment film such as a polyimide alignment film or the like.

EXAMPLES

The present invention is more specifically described below based on examples, but the present invention is not limited to these examples.

Example 1

In a reactor provided with a stirrer, a condenser, and a thermometer, 10 g of 3-fluoro-4-(1-decyloxyoxy)phenyl boronic acid, 5.3 g of bromophenol, 8.5 g of potassium carbonate, 100 mg of tetrakis-triphenylphosphine palladium, and 100 ml of ethanol were added and reacted at 90° C. for 5 hours. After the completion of reaction, the reaction product was cooled, and then 200 ml of ethyl acetate was added. Then, an organic layer was washed with water and saturated saline, and the solvent was distilled off, and the residue was recrystallized with toluene to produce 9 g of a compound represented by (1).

[Chem. 32]

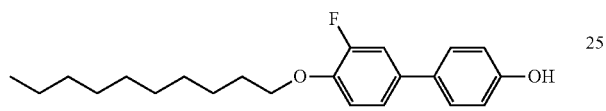

(1)

Next, 9 g of the compound (1), 10 g of 5-(bromomethyl)-2,2-dimethyl-1,3-dioxan-5-yl) methanol, 8 g of potassium carbonate, and 50 ml of N,N-dimethylformamide were added and reacted at 90° C. for 5 hours. After the completion of reaction, the reaction product was cooled, and 200 ml of ethyl acetate was added. Then, an organic layer was washed with water and saturated saline, and the solvent was distilled off. Then, the residue was dispersed and washed with toluene and then purified by an alumina column to produce 11 g of a compound represented by formula (2).

[Chem. 33]

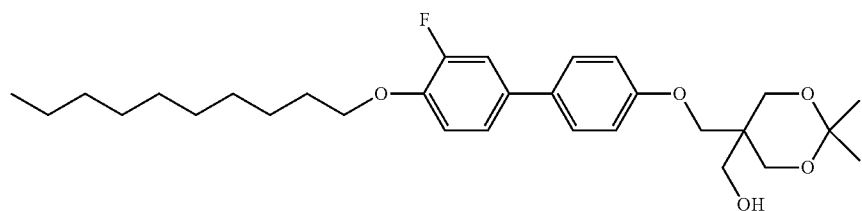

(2)

Next, in a reactor provided with a stirrer, a condenser, and a thermometer, 42 g of the compound (3), 2.5 g of triethylamine, and 50 ml of dichloromethane were added, and then the reactor was cooled to 10° C. or less. Then, 2.5 g of methacryloyl chloride was slowly added dropwise. After the completion of addition, the reactor was returned to room temperature, followed by reaction for 3 hours. After the completion of reaction, water was slowly added, and the resultant mixture was washed with 100 ml of dichloromethane, water, and saturated saline. The solvent was distilled off, and the residue was purified by an alumina column to produce 12 g of a compound represented by (3).

[Chem. 34]

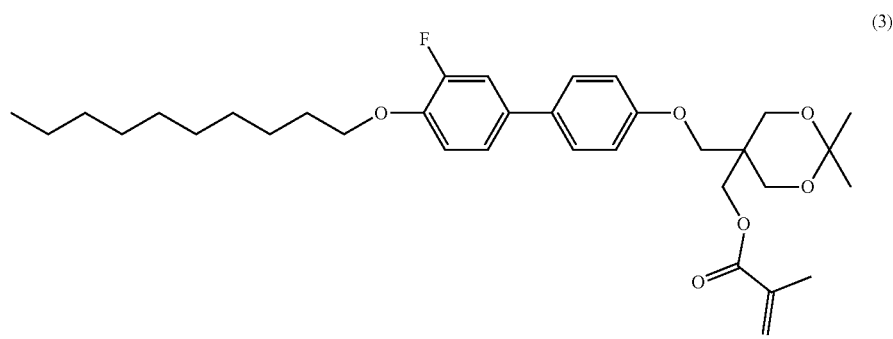

(3)

Then, in a reactor provided with a stirrer and a thermometer, the compound (4) and 100 ml of THF were added, and 20 ml of 10% hydrochloric acid was slowly added dropwise. After the completion of reaction, the reaction product was cooled, and a target material was extracted with ethyl acetate. An organic layer was washed with water and saturated saline, and the solvent was distilled off. Then, the residue was dispersed and washed with toluene and purified by an alumina column to produce 8 g of a target compound represented by formula (4).

[Chem. 35]

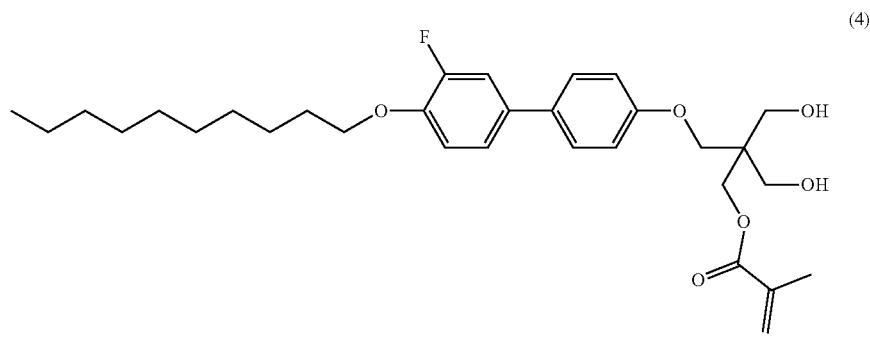

(4)

(Physical Property Values)

Melting point 79° C.

$^1$H-NMR (solvent: deuterated chloroform): δ: 0.88 (t, 3H), 1.29-1.31 (m, 12H), 1.44-1.49 (m, 2H), 1.83 (m, 2H), 1.97 (s, 3H), 2.55 (s, 2H), 3.77-3.86 (m, 4H), 4.05 (t, 4H), 4.38 (s, 2H), 5.60 (s, 1H), 6.14 (s, 1H), 6.95 (m, 3H), 7.20-7.27 (m, 2H), 7.46 (d, 2H)

$^{13}$C-NMR (solvent: deuterated chloroform): δ: 14.1, 17.3, 22.7, 25.9, 27.9, 29.6, 31.8, 45.3, 62.5, 64.0, 68.7, 114.7, 122.3, 125.2, 128.4, 135.5, 138.6, 146.7, 152.7, 158.3, 166.0

Example 2

In a reactor provided with a stirrer, a condenser, and a thermometer, 13 g of 2-fluoro-4-(trans-4-pentylcychexyl) phenyl boronic acid, 12 g of bromophenol, 10 g of potassium carbonate, 150 mg of tetrakis-triphenylphosphine palladium, and 150 ml of ethanol were added and reacted at 90° C. for 5 hours. After the completion of reaction, the reaction product was cooled, and then 200 ml of ethyl acetate was added. Then, an organic layer was washed with water and saturated saline, and the solvent was distilled off, and the residue was recrystallized with toluene to produce 13.5 g of a compound represented by (5).

[Chem. 36]

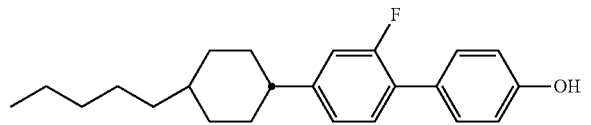

(5)

Next, 13.5 g of the compound (5), 12 g of 5-(bromomethyl)-2,2-dimethyl-1,3-dioxan-5-yl) methanol, 4.5 g of potassium carbonate, and 100 ml of N,N-dimethylformamide were added and reacted at 90° C. for 5 hours. After the completion of reaction, the reaction product was cooled, and 250 ml of ethyl acetate was added. Then, an organic layer was washed with water and saturated saline, and the solvent was distilled off. Then, the residue was dispersed and washed with toluene and then purified by an alumina column to produce 11 g of a compound represented by formula (2).

[Chem. 37]

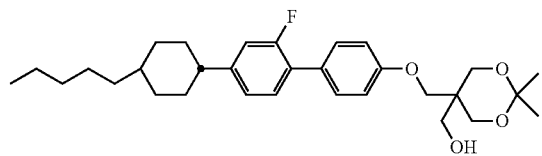

(6)

Next, in a reactor provided with a stirrer, a condenser, and a thermometer, 11 g of the compound (6), 2.4 g of triethylamine, and 100 ml of dichloromethane were added, and then the reactor was cooled to 10° C. or less. Then, 3.4 g of methacryloyl chloride was slowly added dropwise. After the completion of addition, the reactor was returned to room temperature, followed by reaction for 3 hours. After the completion of reaction, water was slowly added, and the resultant mixture was washed with 100 ml of dichloromethane, water, and saturated saline. The solvent was distilled off, and the residue was purified by an alumina column to produce 12 g of a compound represented by (7).

[Chem. 38]

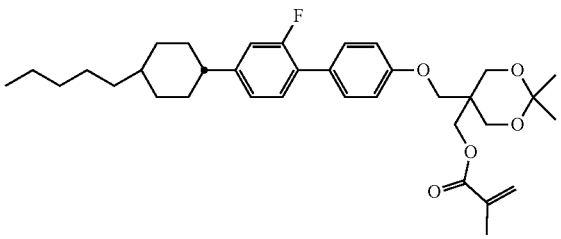

(7)

Then, in a reactor provided with a stirrer and a thermometer, the compound (4) and 100 ml of THF were added, and 20 ml of 10% hydrochloric acid was slowly added dropwise. After the completion of reaction, the reaction product was cooled, and a target material was extracted with ethyl acetate. An organic layer was washed with water and saturated saline, and the solvent was distilled off. Then, the residue was dispersed and washed with toluene and purified by an alumina column to produce 8 g of a target compound represented by formula (8).

[Chem. 39]

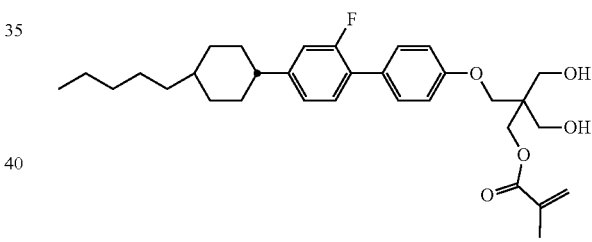

(8)

(Physical Property Values)

Melting point 113° C.

$^1$H-NMR (solvent: deuterated chloroform): δ: 0.88 (t, 3H), 1.28-1.31 (m, 8H), 1.34-1.38 (m, 4H), 1.49 (m, 1H), 1.83-1.86 (m, 4H), 1.97 (s, 3H), 2.55 (s, 2H), 2.72 (m, 1H), 3.77-3.86 (m, 4H), 4.05 (m, 2H), 4.38 (s, 2H), 5.60 (s, 1H), 6.14 (d, 2H), 6.95 (m, 2H), 7.20-7.27 (m, 3H)

$^{13}$C-NMR (solvent: deuterated chloroform): δ: 14.1, 17.3, 22.7, 25.9, 27.9, 29.6, 31.8, 37.1, 31.0, 31.1, 45.3, 62.5, 64.5, 68.7, 114.0, 114.9, 125.3, 129.1, 129.7, 135.5, 136.0, 138.6, 158.3, 166.0

Example 3

In a reactor provided with a stirrer, a condenser, and a thermometer, 13.5 g of the compound (5) was dissolved in 100 ml of dichloromethane. Then, 20 ml of a dichloromethane solution in which 7 g of bromine had been dissolved was slowly added dropwise while the reactor was heated to 40° C. After the completion of addition, the resultant mixture was reacted at 40° C. for 4 hours. After the completion of reaction, excessive bromine was decomposed with sodium hydrogen sulfite, and then 200 ml of dichloromethane was added. An organic layer was washed with water and saturated saline, and the solvent was distilled off. The residue was recrystallized with toluene to produce 15 g of a compound represented by formula (9).

[Chem. 40]

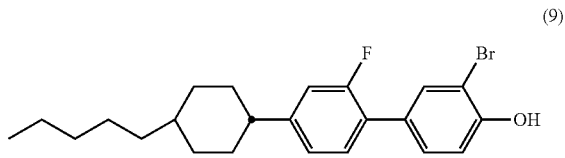
(9)

Next, 15 g of the compound (9), 13 g of 5-(bromomethyl)-2,2-dimethyl-1,3-dioxan-5-yl) methanol, 8 g of potassium carbonate, and 150 ml of N,N-dimethylformamide were added and reacted at 90° C. for 5 hours. After the completion of reaction, the reaction product was cooled, and 250 ml of ethyl acetate was added. Then, an organic layer was washed with water and saturated saline, and the solvent was distilled off. Then, the residue was dispersed and washed with toluene and then purified by an alumina column to produce 16 g of a compound represented by formula (10).

[Chem. 41]

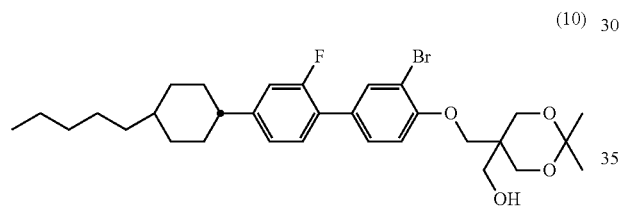
(10)

Next, in a reactor provided with a stirrer, a condenser, and a thermometer, 16 g of the compound (10), 50 ml of triethylamine, and 0.5 g of copper iodide were added and then heated to 60° C. Then, 2.0 g of propargyl alcohol was slowly added dropwise. After the completion of addition, the resultant mixture was reacted for 1 hour. After the completion of reaction, the reaction product was cooled, and 100 ml of tetrahydrofuran and 250 ml of ethyl acetate were added. Then, an organic layer was washed with water and saturated saline, and the solvent was distilled off. Then, the residue was dispersed and washed with toluene and purified by an alumina column to produce 11 g of a compound represented by formula (11).

[Chem. 42]

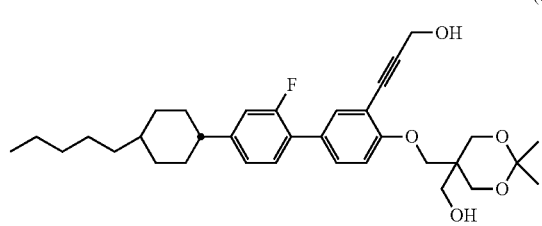
(11)

Then, in a 300-ml autoclave, 11 g of the compound (11), 500 mg of 5% palladium carbon (hydrous product), and 100 ml of tetrahydrofuran were added, and contact hydrogen reduction was performed under a hydrogen pressure of 0.5 kPa. After the completion of reaction, the palladium carbon was filtered off, and then the residue was dispersed and washed with toluene and purified by an alumina column to produce 10 g of a compound represented by formula (12).

[Chem. 43]

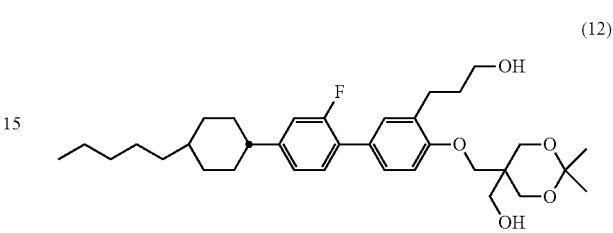
(12)

Next, in a reactor provided with a stirrer, a condenser, and a thermometer, 11 g of the compound (12), 2.0 g of triethylamine, and 100 ml of dichloromethane were added, and the reactor was cooled to 10° C. or less. Then, 2.2 g of methacryloyl chloride was slowly added dropwise. After the completion of reaction, the reactor was returned to room temperature, followed by reaction for 3 hours. After the completion of reaction, water was slowly added, and the resultant mixture was washed with 100 ml of dichloromethane, water, and saturated saline. The solvent was distilled off, and then the residue was purified by an alumina column to produce 11 g of a compound represented by (13).

[Chem. 44]

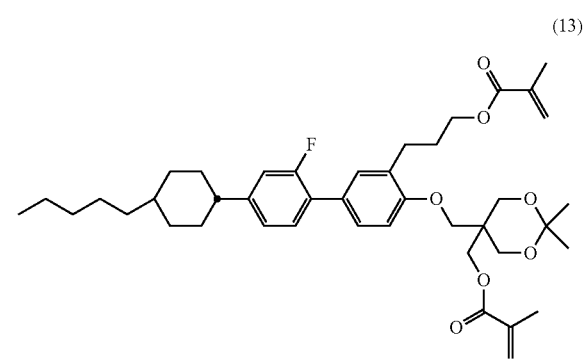
(13)

Then, in a reactor provided with a stirrer and a thermometer, 11 g of the compound (13) and 100 ml of THF were added, and 20 ml of 10% hydrochloric acid was slowly added dropwise. After the completion of reaction, the reaction product was cooled, and a target material was extracted with ethyl acetate. An organic layer was washed with water and saturated saline, and the solvent was distilled off. Then, the residue was dispersed and washed with toluene and purified by an alumina column to produce 9 g of a target compound represented by formula (14).

[Chem. 45]

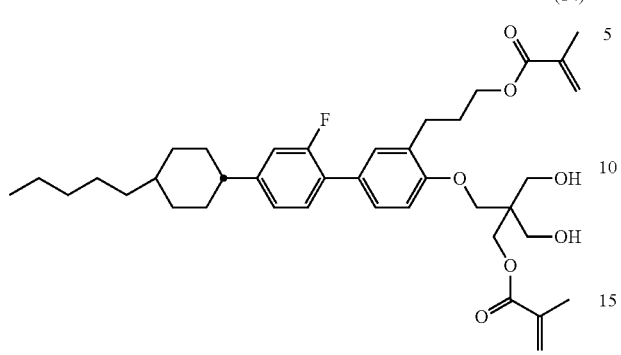
(14)

(Physical Property Values)
Oily
¹H-NMR (solvent: deuterated chloroform): δ: 0.88 (t, 3H), 1.28-1.31 (m, 8H), 1.34-1.38 (m, 4H), 1.49 (m, 1H), 1.83-1.86 (m, 6H), 1.97 (s, 6H), 2.55 (s, 2H), 2.63 (t, 2H), 2.72 (m, 1H), 3.77-3.86 (m, 4H), 4.05 (m, 2H), 4.20 (t, 2H), 4.38 (s, 2H), 5.60 (s, 1H), 6.14 (d, 2H), 6.95 (m, 2H), 7.20-7.27 (m, 1H), 7.82 (m, 1H)
¹³C-NMR (solvent: deuterated chloroform): δ: 14.1, 17.3, 22.7, 25.9, 26.3, 27.9, 29.6, 30.6, 31.8, 37.1, 31.0, 31.1, 45.3, 62.5, 64.5, 68.7, 114.0, 114.9, 125.3, 129.1, 129.7, 135.5, 136.0, 138.6, 158.3, 166.0

Example 4

In a reactor provided with a stirrer, a condenser, and a thermometer, 9 g of the compound (14) of Example 3 and 100 ml of dichloromethane were added and cooled to 10° C. or less. Then, 3.5 g of ethyl chloroformate was slowly added dropwise. After the completion of addition, the resultant mixture was stirred for 30 minutes. Next, 3.6 g of triethylamine was added dropwise. After the completion of reaction, an organic layer was washed with water and saturated saline, and the solvent was distilled off. Then, the residue was purified by a silica column to produce 8 g of a target compound represented by compound (15).

[Chem. 46]

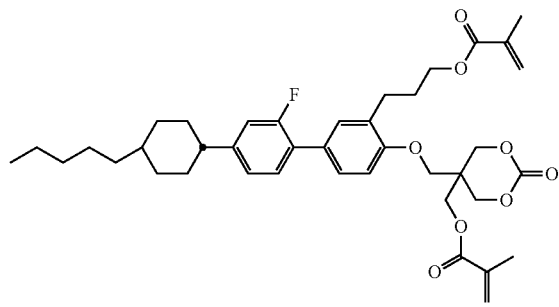
(15)

(Physical Property Values)
Melting point 42° C.
¹H-NMR (solvent: deuterated chloroform): δ: 0.88 (t, 3H), 1.28-1.31 (m, 8H), 1.34-1.38 (m, 4H), 1.49 (m, 1H), 1.83-1.86 (m, 6H), 1.97 (s, 6H), 2.63 (m, 1H), 2.72 (m, 2H), 3.77-3.89 (m, 4H), 4.05 (m, 2H), 4.20 (t, 2H), 4.38 (s, 2H), 5.55 (s, 1H), 5.60 (s, 1H), 6.14 (d, 2H), 6.83 (d, 1H), 6.95 (m, 2H), 6.90-7.09 (m, 2H), 7.30-7.34 (m, 1H), 7.36-7.48 (m, 2H)
¹³C-NMR (solvent: deuterated chloroform): δ: 14.1, 17.3, 22.7, 25.9, 26.3, 27.9, 29.6, 30.6, 31.8, 37.1, 31.0, 31.1, 45.3, 62.5, 64.5, 68.7, 74.1, 114.0, 114.9, 125.3, 129.1, 129.7, 135.5, 136.0, 138.6, 158.3, 157.2, 166.0

Example 5

Seven g of a target compound represented by compound (17) was produced by the same method as in Example 3 except that 15.5 of the compound (16) was used in place of 13.5 g of the compound (5) used in Example 3.

[Chem. 47]

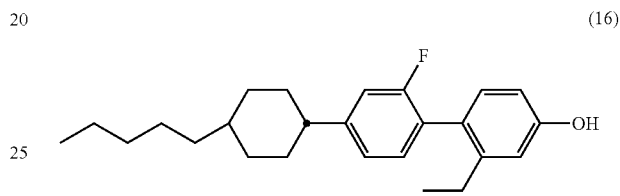
(16)

[Chem. 48]

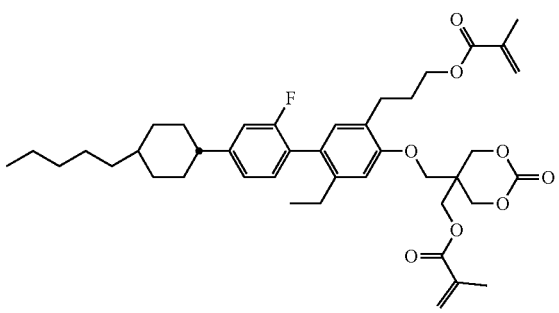
(17)

(Physical Property Values)
Melting point 85° C.
¹H-NMR (solvent: deuterated chloroform): δ: 0.88 (t, 3H), 1.07-1.09 (m, 5H), 1.24-1.33 (m, 10H), 1.49 (m, 1H), 1.87-1.96 (m, 12H), 2.63 (m, 3H), 2.69 (m, 2H), 4.10 (s, 2H), 4.17 (t, 2H), 4.38 (s, 2H), 4.45-4.56 (m, 4H), 5.55 (s, 1H), 5.60 (s, 1H), 6.14 (d, 2H), 6.74 (s, 1H), 6.93-7.01 (m, 3H), 7.25 (t, 1H)
¹³C-NMR (solvent: deuterated chloroform): δ: 14.1, 17.3, 22.7, 25.9, 26.3, 27.9, 28.4, 29.6, 30.4, 30.6, 31.8, 37.1, 31.0, 31.1, 45.3, 62.5, 64.5, 68.7, 74.1, 114.0, 114.9, 125.3, 129.1, 129.7, 135.5, 136.0, 138.6, 158.3, 157.2, 166.0

A liquid crystal composition was prepared by using each of the resultant compounds as follows, and an evaluation test was performed. The evaluation test is as follows.
(Evaluation Test of Low-Temperature Storability)
The liquid crystal composition was filtered with a membrane filter (manufactured by Agilent Technologies, Inc., PTFE 13 mm-0.2 μm) and allowed to stand for 15 minutes under the vacuum reduced-pressure condition to remove dissolved air. Then, 0.5 g of the liquid crystal composition was weighed in a vial bottle washed with acetone and sufficiently dried, and then allowed to stand for 7 days in an environment of −15° C. Then, the presence of precipitate was visually observed.

(Test of Vertical Alignment)

The liquid crystal composition was dropped on a transparent electrode substrate without an alignment film and held between the transparent electrode substrate and another transparent electrode substrate, and then a sealing material was cured to form a liquid crystal display device having a cell gap of 3.2 μm. In this case, vertical alignment was determined by visual observation according to the following four levels.

Level A: Uniform vertical alignment
Level B: Allowable level of slight alignment defect
Level C: Unallowable level of alignment defect
Level D: Very poor alignment defect (Example 6) Preparation of Liquid Crystal Composition A host liquid crystal (H) showing physical property values described below was prepared. All the values are measured values.
$T_{n-i}$(nematic-isotropic liquid phase transition temperature): 73.8° C.
Δε (dielectric anisotropy at 25° C.): −2.79
Δn (refractive index anisotropy at 25° C.): 0.101
$γ_1$ (rotational viscosity coefficient at 25° C.): 118

A composition LC-1 was prepared by adding 0.3% by weight of a polymerizable compound (P-2-8) below to 100% by weight of the host liquid crystal (H).

[Chem. 49]

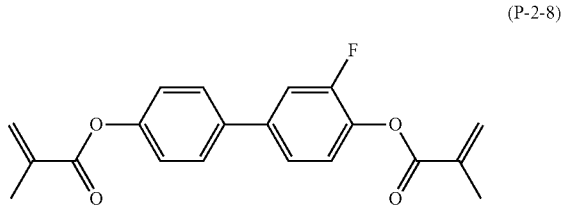

(P-2-8)

Further, a liquid crystal composition (LC-1M1) was prepared by adding 0.5% by weight of the compound (4) synthesized in Example 1 to 100% by weight of the liquid crystal composition (LC-1).

[Chem. 50]

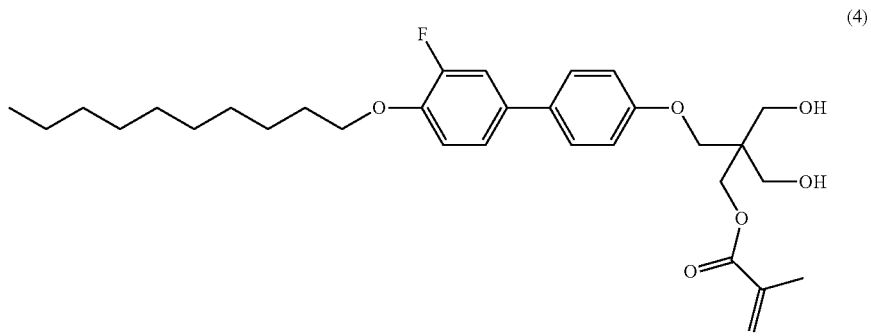

(4)

The liquid crystal composition (LC-1M1) was injected into a glass cell without an alignment film and then heated at 120° C. for 1 hour. Then, the observation of alignment showed uniform vertical alignment (Level A). Further, as a result of test of low-temperature storage stability, precipitate was not observed even after storage at −15° C. for 1 week, and thus excellent storage stability was exhibited.

(Example 7) Preparation of Liquid Crystal Composition

A liquid crystal composition (LC-1M2) was prepared by adding 0.5% by weight of the compound (17) synthesized in Example 5 to 100% by weight of the liquid crystal composition (LC-1).

The liquid crystal composition (LC-1M2) was injected into a glass cell without an alignment film and then heated at 120° C. for 1 hour. Then, the observation of alignment showed uniform vertical alignment (Level A). Further, as a result of test of low-temperature storage stability, precipitate was not observed even after storage at −15° C. for 1 week, and thus excellent storage stability was exhibited.

Comparative Example 1

A liquid crystal composition (LC-1M3) was prepared by adding 0.5% by weight of the compound represented by formula (16) below to 100% by weight of the liquid crystal composition (LC-1).

[Chem. 51]

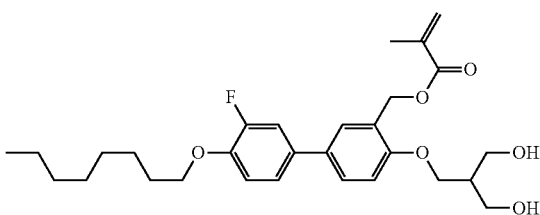

(16)

The liquid crystal composition (LC-1M3) was injected into a glass cell without an alignment film and then heated at 120° C. for 1 hour. Then, the observation of alignment showed vertical alignment (Level B). Further, as a result of test of storage stability of (LC-1M2), precipitate was observed at 2nd day at −15° C., and thus unsatisfactory results were exhibited.

Comparative Example 2

A liquid crystal composition (LC-1M4) was prepared by adding 0.5% by weight of the compound represented by formula (17) below to 100% by weight of the liquid crystal composition (LC-1).

[Chem. 52]

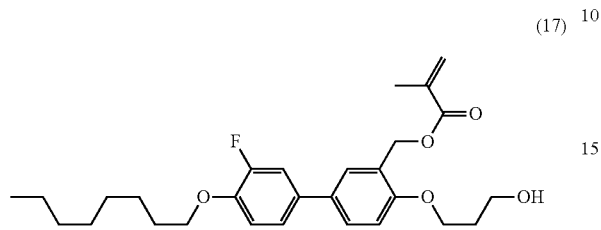
(17)

The liquid crystal composition (LC-1M4) was injected into a glass cell without an alignment film and then heated at 120° C. for 1 hour. Then, the observation of alignment showed an unallowable level of alignment (Level C) with alignment defects. Further, as a result of test of storage stability of (LC-1M2), precipitate was not observed after storage at −15° C. for 1 week.

As described above, the compounds of the present invention have both the alignment and storage stability, and thus an excellent liquid crystal composition can be provided.

The invention claimed is:

1. A compound represented by general formula (i),

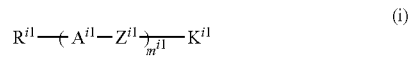
(i)

(in the formula, $R^{i1}$ represents a hydrogen atom, a linear or branched alkyl group having 1 to 40 carbon atoms, an alkyl halide group, or $P^{i1}$-$Sp^{i1}$-, in which —$CH_2$— in the alkyl group in the linear or branched alkyl group or the alkyl halide group may be substituted by —CH=CH—, —C≡C—, —O—, —NH—, —COO—, or —OCO— so that oxygen atoms are not directly adjacent to each other; $A^{i1}$ represents a divalent 6-membered aromatic cyclic group, a divalent 6-membered aromatic heterocyclic group, a divalent 6-membered aliphatic cyclic group, or a divalent 6-membered aliphatic heterocyclic group, in which a hydrogen atom in a cyclic structure of $A^{i1}$ may be substituted by a halogen atom, $P^{i1}$-$Sp^{i1}$-, a monovalent organic group having a substituent represented by $K^{i1}$, or $R^{i1}$; $Z^{i1}$ represents a single bond, —CH=CH—, —CF=CF—, —C≡C—, —COO—, —OCO—, —OCOO—, —OOCO—, —$CF_2$O—, —O$CF_2$—, —CH=CHCOO—, —OCOCH=CH—, —CH=C($CH_3$)COO—, —OCOC($CH_3$)=CH—, —$CH_2$—CH($CH_3$)COO—, —OCOCH($CH_3$)—$CH_2$—, —O$CH_2$$CH_2$O—, or an alkylene group having 2 to 20 carbon atoms, in which one or two or more nonadjacent —$CH_2$— may be substituted by —O—, —COO—, or —OCO—; $K^{i1}$ represents a group represented by general formulae (K-1) to (K-3); $X^{K1}$ and $Y^{K1}$ each independently represent —$CH_2$—, an oxygen atom, or a sulfur atom; $Z^{K1}$ represents an oxygen atom or a sulfur atom; $S^1$, $S^3$, $S^4$, and $S^5$ each represent an alkylene group having 1 to 6 carbon atoms or a single bond; $S^2$ represents C, or Si; $X^1$ and $X^2$ each represent OH, —$NH_2$, —$NHR^{i1}$, —CHO, —COOH, or —SH; P and $P^{i1}$ each represent a polymerizable group; $Sp^{i1}$ represents a spacer group or a single bond; $m^{i1}$ represents an integer of 2 to 4; n represents 1; when a plurality of each of $R^{i1}$, $A^{i1}$, $Z^{i1}$, $K^{i1}$, $X^{K1}$, $Y^{K1}$, $Z^{K1}$, $S^1$, $S^2$, $S^3$, $S^4$, $S^5$, $p^{i1}$, $Sp^{i1}$, and n are present in the general formula (i), they may be the same or different)

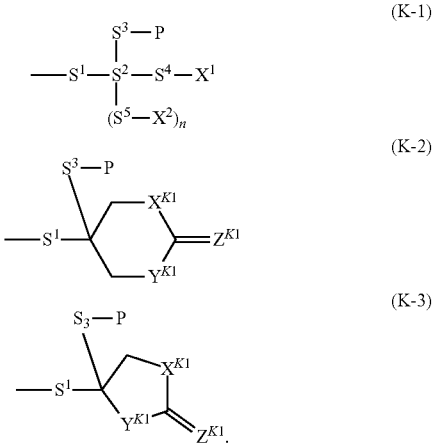

2. The compound according to claim 1, wherein in the general formula (i), $A^{i1}$ represents a group having a cyclic structure selected from a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indane-2,5-diyl group, a 1,2,3,4-tetrahydronaphthalene-2,6-diyl group, and a 1,3-dioxane-2,5-diyl group, in which the cyclic structure may be unsubstituted or substituted by an alkyl group having 1 to 12 carbon atoms, an alkyl halide group having 1 to 12 carbon atoms, an alkoxy group having 1 to 12 carbon atoms, an alkoxy halide group having 1 to 12 carbon atoms, a halogen atom, or $P^{i1}$-$Sp^{i1}$-.

3. The compound according to claim 1, wherein $P^{i1}$-$Sp^{i1}$- represents a substituent selected from the group represented by general formula (P-1) to general formula (P-14) below,

(P-1)

(P-2)

(P-3)

(P-4)

(P-5)

-continued

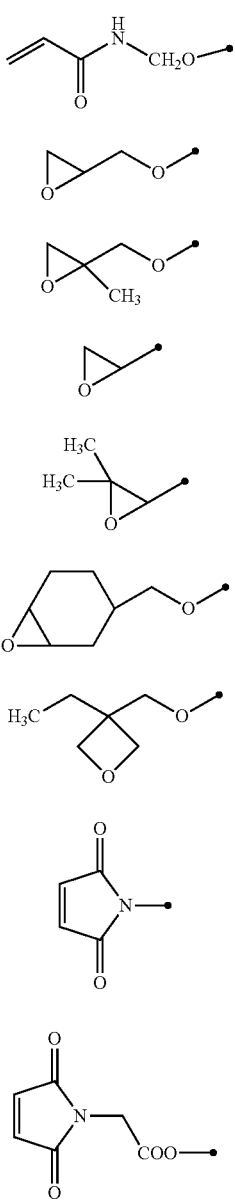

(P-6)
(P-7)
(P-8)
(P-9)
(P-10)
(P-11)
(P-12)
(P-13)
(P-14)

(in the formulae, a black spot at the right end represents a bond).

4. The compound according to claim 1, wherein in the general formula (i), $K^{i1}$ represents (K-1), (K-1)

(iii)

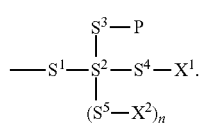

5. The compound according to claim 4, wherein $S^4$ and $S^5$ each represent the alkylene group having 1 to 6 carbon atoms, and $X^i$ and $X^2$ each represent —OH.

6. The compound according to claim 1, wherein in the general formula (i), $K^{i1}$ represents (K-2):

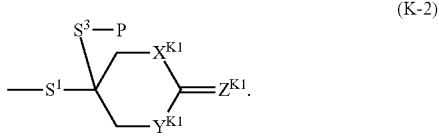
(K-2)

7. The compound according to claim 1, wherein in the general formula (i), $K^{i1}$ represents (K-1),

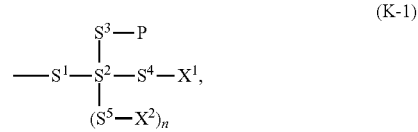
(K-1)

wherein a hydrogen atom in a cyclic structure of at least one $A^{i1}$ is substituted by $P^{i1}$-$Sp^{i1}$-.

8. A liquid crystal composition comprising the compound according to claim 1, a polymerizable compound, and a nonpolymerizable liquid crystal composition.

9. The liquid crystal composition according to claim 8, comprising, as the polymerizable compound, one or two or more compounds represented by general formula (P),

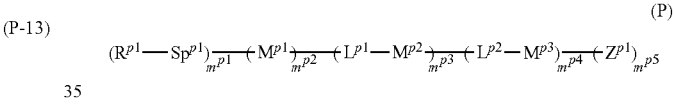
(P)

(in the formula,
$Z^{p1}$ represents a fluorine atom, a cyano group, a hydrogen atom, an alkyl group having 1 to 15 carbon atoms, in which a hydrogen atom may be substituted by a halogen atom, an alkoxy group having 1 to 15 carbon atoms, in which a hydrogen atom may be substituted by a halogen atom, an alkenyl group having 1 to 15 carbon atoms, in which a hydrogen atom may be substituted by a halogen atom, an alkenyloxy group having 1 to 15 carbon atoms, in which a hydrogen atom may be substituted by a halogen atom, or -$Sp^{p2}$—$R^{p2}$
$R^{p1}$ and $R^{p2}$ each represent any one of the following formula (R-I) to formula (R-VIII):

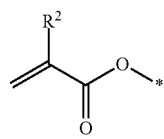
(R-I)

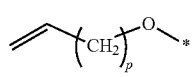
(R-II)

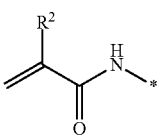
(R-III)

-continued

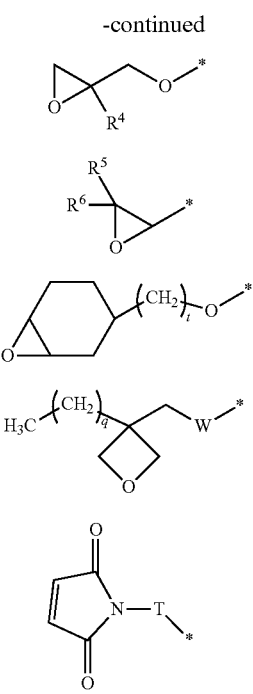

(R-IV)

(R-V)

(R-VI)

(R-VII)

(R-VIII)

(in the formulae,
* represents a bond to $Sp^{p1}$ or $Sp^{p2}$
$R^2$ to $R^6$ each independently represent a hydrogen atom, an alkyl group having 1 to 5 carbon atoms, or an alkyl halide group having 1 to 5 carbon atoms;
W represents a single bond, —O—, or a methylene group;
T represents a single bond or —COO—; and
p, t, and q each independently represent 0, 1, or 2);
$Sp^{p1}$ and $Sp^{p2}$ each represent a spacer group;
$L^{p1}$ and $L^{p2}$ each independently represent a single bond, —O—, —S—, —CH$_2$—, —OCH$_2$—, —CH$_2$O—, —CO—, —C$_2$H$_4$—, —COO—, —OCO—, —OCOOCH$_2$—, —CH$_2$OCOO—, —OCH$_2$CH$_2$O—, —CO—NR$^a$—, —NR$^a$—CO—, —SCH$_2$—, —CH$_2$S—, —CH=CR$^a$—COO—, —CH=CR$^a$—OCO—, —COO—CR$^a$=CH—, —OCO—CR$^a$=CH—, —COO—CR$^a$=CH—COO—, —COO—CR$^a$=CH—OCO—, —OCO—CR$^a$=CH—COO—, —OCO—CR$^a$=CH—OCO—, —(CH$_2$)z-C(=O)—O—, —(CH$_2$)z-O—(C=O)—, —O—(C=O)—(CH$_2$)z-, —(C=O)—O—(CH$_2$)z-, —CH$_2$(CH$_3$)C—C(=O)—O—, —CH$_2$(CH$_3$)C—O—(C=O)—, —O—(C=O)—C(CH$_3$)CH$_2$, —(C=O)—O—C(CH$_3$)—CH$_2$, —CH=CH—, —CF=CF—, —CF=CH—, —CH=CF—, —CF$_2$—, —CF$_2$O—, —OCF$_2$—, —CF$_2$CH$_2$—, —CH$_2$CF$_2$—, —CF$_2$CF$_2$—, or —C≡C— (wherein R$^a$ each independently represent a hydrogen atom or an alkyl group having 1 to 4 carbon atoms, and z represents an integer of 1 to 4);
Mp$^2$ represents a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indane-2,5-diyl group, a 1,2,3,4-tetrehydronaphthalene-2,6-diyl group, a 1,3-dioxane-2,5-diyl group, or a single bond, and Mp$^2$ is may be unsubstituted or substituted by an alkyl group having 1 to 12 carbon atoms, an alkyl halide group having 1 to 12 carbon atoms, an alkoxy group having 1 to 12 carbon atoms, an alkoxy halide group having 1 to 12 carbon atoms, a halogen atom, a cyano group, a nitro group, or —R$^{p1}$;

M$^{p1}$ represents any one of the following formulae (i-11) to (ix-11):

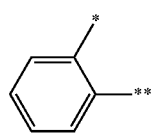
(i-11)

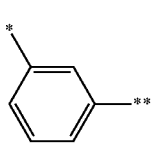
(ii-11)

(iii-11)

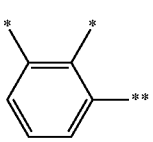
(iv-11)

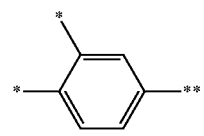
(v-11)

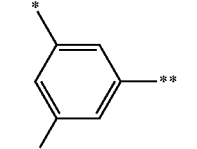
(vi-11)

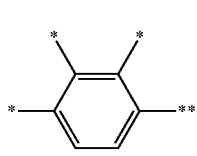
(vii-11)

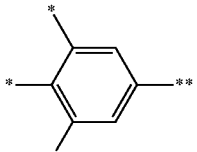
(viii-11)

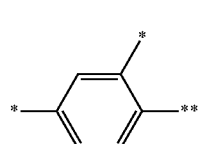
(ix-11)

(in the formulae, * represents a bond to $Sp^{p1}$, and ** represents a bond to $L^{p1}$, $L^{p2}$, or $Z^{p1}$);

$MP^3$ represents any one of the following formulae (i-13) to (ix-13):

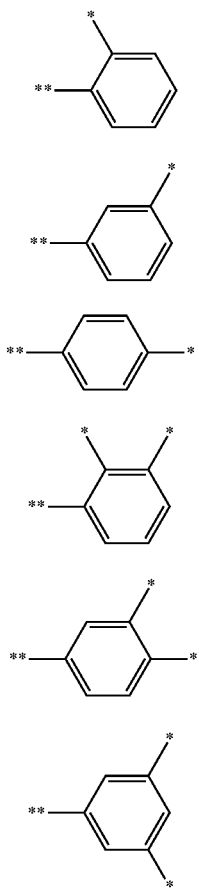

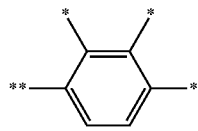

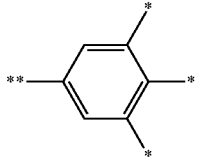

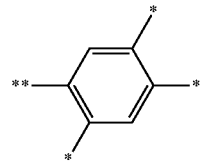

(in the formulae, * represents a bond to $Z^{p1}$, and ** represents a bond to $L^{p2}$);

$m^{p2}$ to $m^{p4}$ each independently represent 0, 1, 2, or 3; $m^{p1}$ and $m^{p5}$ each independently represent 1, 2, or 3; when a plurality of $Z^{p1}$ are present, they may be the same or different; when a plurality of $R^{p1}$ are present, they may be the same or different; when a plurality of $RP^2$ are present, they may be the same or different; when a plurality of $Sp^p i$ are present, they may be the same or different; when a plurality of $Sp^{p2}$ are present, they may be the same or different; when a plurality of $L^{p1}$ are present, they may be the same or different; and when a plurality of $MP^{p2}$ are present, they may be the same or different).

10. A liquid crystal display device comprising the liquid crystal composition according to claim and two substrates at least one of which does not have an alignment film.

* * * * *